United States Patent
Sakai et al.

(10) Patent No.: US 8,684,938 B2
(45) Date of Patent: Apr. 1, 2014

(54) APPARATUS FOR EVALUATING BIOLOGICAL CONDITION, METHOD FOR THE SAME, AND COMPUTER PROGRAM PRODUCT

(75) Inventors: Kazuhiro Sakai, Toyoake (JP); Shinji Nanba, Kariya (JP); Takao Katoh, Tokyo (JP); Motohisa Osaka, Musashino (JP); Yoshitaka Fuwamoto, Toyota (JP)

(73) Assignees: DENSO CORPORATION, Kariya (JP); Nippon Medical School Foundation, Tokyo (JP); Toyota Jidosha Kabushiki Kaisha, Toyota (JP)

( * ) Notice: Subject to any disclaimer, the term of this patent is extended or adjusted under 35 U.S.C. 154(b) by 1060 days.

(21) Appl. No.: 12/688,994

(22) Filed: Jan. 18, 2010

(65) Prior Publication Data
US 2010/0185101 A1    Jul. 22, 2010

(30) Foreign Application Priority Data
Jan. 19, 2009    (JP) .................................... 2009-9070

(51) Int. Cl.
*A61B 5/0205*    (2006.01)
*A61B 5/024*    (2006.01)

(52) U.S. Cl.
USPC ............ 600/483; 600/481; 600/500; 600/509

(58) Field of Classification Search
USPC ................................................ 600/481–526
See application file for complete search history.

(56) References Cited

U.S. PATENT DOCUMENTS

| | | | | |
|---|---|---|---|---|
| 4,832,038 A | * | 5/1989 | Arai et al. | 600/483 |
| 5,042,497 A | * | 8/1991 | Shapland | 600/509 |
| 5,437,285 A | * | 8/1995 | Verrier et al. | 600/515 |
| 5,682,901 A | * | 11/1997 | Kamen | 600/519 |
| 5,813,989 A | * | 9/1998 | Saitoh et al. | 600/484 |
| 5,891,044 A | * | 4/1999 | Golosarsky et al. | 600/509 |
| 7,113,824 B2 | * | 9/2006 | Krig et al. | 607/14 |

(Continued)

FOREIGN PATENT DOCUMENTS

| | | |
|---|---|---|
| JP | H11-195198 A | 7/1999 |
| JP | 3729143 B2 | 10/2005 |

OTHER PUBLICATIONS

Bettoni et al. "Autonomic Tone Variations Before the Onset of Paroxysmal Atrial Fibrillation." Circulation. 2002;105:2753-2759.*

(Continued)

*Primary Examiner* — Navin Natnithithadha
*Assistant Examiner* — Meredith Weare
(74) *Attorney, Agent, or Firm* — Posz Law Group, PLC

(57) ABSTRACT

A biological condition evaluation apparatus determines a symptom of a heart abnormality based on at least one index calculated from a heartbeat interval and/or a pulse interval. The apparatus determines whether it is in a referential period where an amount of change in the index is comparatively small. The apparatus determines whether a plurality of conditions are satisfied or not in an evaluation period set after the referential period. One condition is that an amount of change in the index in the evaluation period is greater than that observed during the referential period. Another condition is that a rate of change in the index is equal to or greater than a predetermined threshold value. The apparatus determines that there is a symptom of a heart abnormality, when both the conditions are satisfied.

20 Claims, 11 Drawing Sheets

(56) References Cited

U.S. PATENT DOCUMENTS

| | | | |
|---|---|---|---|
| 7,227,955 B2 | 6/2007 | Trifonov et al. | |
| 7,413,548 B2 | 8/2008 | Tadokoro et al. | |
| 7,572,226 B2* | 8/2009 | Scheiner et al. | 600/485 |
| 7,945,313 B2* | 5/2011 | Fuwamoto et al. | 600/509 |
| 2004/0111033 A1* | 6/2004 | Oung et al. | 600/483 |
| 2004/0236236 A1* | 11/2004 | Yanagidaira et al. | 600/509 |
| 2005/0148894 A1* | 7/2005 | Misczynski et al. | 600/513 |
| 2006/0025698 A1* | 2/2006 | Nakagawa et al. | 600/513 |
| 2006/0074451 A1* | 4/2006 | Chen et al. | 607/3 |
| 2007/0265540 A1* | 11/2007 | Fuwamoto et al. | 600/515 |
| 2008/0071177 A1* | 3/2008 | Yanagidaira et al. | 600/483 |

OTHER PUBLICATIONS

Huang et al. "Changes of autonomic tone before the onset of paroxysmal atrial fibrillation." International Journal of Cardiology 66 (1998) 275-283.*

Shusterman et al. "Autonomic Nervous System Activity and the Spontaneous Initiation of Ventricular Tachycardia."JACC vol. 32, No. 7. Dec. 1998:1891-9.*

"Regression and Correlation." StatsDirect Limited. Mar. 13, 2007. web.archive.org/web/20070313205017/http://www.statsdirect.com/help/regression_and_correlation/rcr.htm.*

Jardine et al. "Cardiac Sympathetic Nerve Activity and Ventricular Fibrillation during Acute Myocardial Infarction an in a Conscious Sheep Model." Am J Physiol Heart Circ Physiol 293:H433-H439, 2007. First published Mar. 16, 2007.*

* cited by examiner

APPARATUS FOR EVALUATING BIOLOGICAL CONDITION, METHOD FOR THE SAME, AND COMPUTER PROGRAM PRODUCT

CROSS REFERENCE TO RELATED APPLICATION

This application is based on Japanese Patent Application No 2009-9070 filed on Jan. 19, 2009, the contents of which are incorporated herein by reference in its entirety.

FIELD OF THE INVENTION

The present invention relates to a biological condition evaluation apparatus which is capable of evaluating a biological condition of a living body, such as a driver of a vehicle, for determining a symptom of abnormalities on the heart, and relates to a method for the same and a computer program product.

BACKGROUND OF THE INVENTION

Some investigation reports that the necessity of measuring a condition of a driver, since automobile incidents are mostly caused by a human factor.

For example, automobile incidents due to an inattentive or napping long-distance truck driver attract some social attention. Automobile incidents due to an abnormality of cardiovascular system also attract social attention. Especially, in the aging society, the abnormalities of the cardiovascular system may attract greater social attention.

For such reasons, the following patent documents 1 and 2 disclose a method of monitoring whether a driver is in a normal condition or an abnormal condition by measuring a heart rate in a vehicle. Those technologies determine whether it is in a normal or an abnormal based on a determination of whether a monitoring value is out of a threshold value or not. In one case, the monitoring value is a high frequency component HF of a heart rate or a heartbeat interval variation HRV. The threshold value is a predetermined value which can be compared with an absolute value of the high frequency component HF. In another case, the monitoring value is an increasing/decreasing rate of the high frequency component HF from an initial stage or an increasing/decreasing rate of the high frequency component HF within a predetermined time period. The threshold value is a predetermined value which can be compared with the increasing/decreasing rates.

The patent document 3 discloses a processing method of electrocardiograph waveform.

The patent document 4 discloses a technology for estimating a heartbeat interval from a heart pulse signal.

Patent Documents

1: US Application Publication 2008/0071177 (WO2005/112764)

2: JPH11-195198A

3: JP2007-301101A

4: JP3729143B

SUMMARY OF THE INVENTION

An increasing/decreasing of the high frequency component HF is monitored in the conventional technology mentioned above. However, the high frequency component HF may be varied greatly according to a behavior of the driver when the driver is in good biological condition and is capable of driving a vehicle normally. Therefore, there may be a possibility to erroneously determine a condition of the driver. For example, even if the driver is in a normal condition, the device may erroneously determine an abnormal condition. If the threshold value is set at an extreme level, it is difficult to detect an abnormality only in an extreme case in advance. Such an extreme threshold value may cause lowering of sensitivity, i.e., accuracy.

It is an object of the present invention to address the above mentioned problem.

It is another object of the present invention to provide an apparatus, a method and a computer readable recording medium, in which a biological condition relating to an abnormality of a heart can be evaluated with high accuracy.

We investigated a record of portable electrocardiograph recorder PECGR in order to find out signs, i.e., symptoms, just before an abnormal condition of a heart. Each of the patients is equipped with the PECGR for 24 hours. In detail, we collected the records of cases for 31 patients and analyzed the records. The records include some incidents of abnormalities of a heart. The incidents include the following four cases. In the first case, the patient died after the patient suffered from a ventricular fibrillation accidentally. In the second case, the patient recovered after the patient suffered from a ventricular fibrillation accidentally, but the ventricular fibrillation was stopped spontaneously. In the third case, the patient died after the patient suffered from a complete heart block. In the fourth case, the patient recovered after the patient suffered from a complete heart block, but the complete heart block was removed spontaneously. We analyzed at least whether the patient was in the first case or the second case, or whether the patient was in the third case or the fourth case.

As a result, we discovered that the electrocardiogram show some distinctive waveform patterns before the patient is suffered from the heart abnormality, and reached to the invention. The electrocardiogram may be referred to as the ECG. In detail, we found a plurality of abnormal waveform patterns on the ECGs. For example, three abnormal waveform patterns can be raised for determining a heart abnormality. The patterns are shown in FIGS. 3A, 3B, 4A, 4B, 5A, and 5B. Hereinafter, the present invention is described in detail.

According to a first aspect of the present invention, an apparatus for evaluating biological condition is provided. The apparatus evaluates a biological condition of a subject to determine a symptom of an abnormality of a heart based on biological information which is at least one of a heartbeat interval RRI and a pulse interval PI. The apparatus includes an index calculating means which calculates a first index by performing the frequency analysis on at least one of the heartbeat interval and the pulse interval. The index indicates the sympathetic nerve activity. For example, the index may be variables indicated with LF/HF in the following embodiments. The apparatus includes a referential period determining means which determines whether it is in a referential period or not. The referential period is a time period in which the index satisfies a predetermined condition which shows that a grade of change in the index calculated in the index calculating means is smaller than a predetermined value, i.e., is within a predetermined range, over a predetermined period. The apparatus includes an abnormality determining means which determines whether the index shows a symptom of an abnormality of a heart or not. The means determines the symptom when the index shows a predetermined waveform in an abnormality evaluation period which is set after the referential period. The predetermined waveform can be detected by determining whether the index shows the following two changes or not. The first change is that an amount of change in the index in increasing and decreasing directions is equal to or greater than a predetermined threshold value which indicates that the amount of change in the index in increasing and decreasing directions is greater than an amount of change in the index observed during the referential period. The second change is that a rate of change in the index in increasing and decreasing directions is equal to or greater than a predetermined threshold value.

The apparatus determines that the index shows a symptom of a heart abnormality when the index shows a predetermined change in an abnormality evaluation period which is set after the referential period. The predetermined change of the index is that a changing range in the index in increasing and decreasing directions is equal to or greater than a predetermined threshold, i.e., is within a predetermined range, and a rate of change in the index in increasing and decreasing directions is equal to or greater than a predetermined threshold.

For example, the apparatus determines that there is a symptom of a heart abnormality when there is, a great change in the index and there is a rapid change in the index, in comparison with change of the index in the referential period, as shown in abnormal patterns in FIGS. 3A to 5B. As a result, it is possible to predict an actual event of a heart abnormality in advance, and therefore, it is possible to detect the heart abnormality with sufficient accuracy.

Other aspects of the present invention are explained below.

In the present invention, an actual heart abnormality, such as ventricular fibrillation, is not determined and detected, but a symptom of the abnormality is determined and detected as an abnormality.

The referential, period corresponds to a condition where it is possible to be considered that there is no heart abnormality. The period of time of the referential period may be predetermined, but may be set variable according to a situation.

The abnormality evaluation period is a period in which an abnormality determination is performed, and it may be set similarly to the referential period. It is not necessary to define the abnormality evaluation period particularly. In such a case, a time period in which an abnormality determination is actually carried out may be considered as an abnormality evaluation period.

Several kinds of conditions may be employed as a predetermined condition which shows that a grade of change in the index in the referential period is small. For example, it is possible to employ a condition which shows that a ratio, i.e., a time period, is smaller than a threshold value, i.e., predetermined value. The ratio may be obtained as a ratio of time in which an amount of change in the index is out of a predetermined threshold with respect to a predetermined period of time.

Several kinds of thresholds may be employed as a predetermined threshold which shows that an amount of change in the index is greater than an amount of change in the index in the referential period. For example, it is possible to employ a value which is greater than an amount of change in the index during the referential period, and a value which is greater than a predetermined range etc., from a center of change in the index during the referential period.

The threshold may be provided with thresholds in both sides in increasing and decreasing directions. In such a case, the threshold may be provided with the same value in increasing and decreasing directions or with different values in increasing and decreasing directions.

The condition which shows that a rate of change in the index in an increasing and decreasing is equal to or greater than a predetermined threshold value may be satisfied when both a rate of change in the index in an increasing direction and a rate of change in the index in a decreasing direction are equal to or greater than the predetermined threshold value. The predetermined threshold value may be provided with different values for the increasing direction and the decreasing direction.

The change in the index in an increasing direction and a decreasing direction means a case in which the index continuously changes from an increasing to a decreasing, and a case in which the index continuously changes from a decreasing to an increasing.

According to another aspect of the invention, the index may be expressed by using the natural logarithm.

Distribution of value of the index is transformed to approximate to the normal distribution by transforming the index by using the natural logarithm. For example, a first index LF/HF and/or a second index HF are transformed.

That is, the absolute value of the index varies greatly depending on individuals. However, the transformation of the natural logarithm allows individual differences to be reduced, and enables an abnormality determination with sufficient accuracy by using the statistical measure.

According to another aspect of the present invention, the predetermined condition for determining the referential period is that a change in the index is equal to or smaller than a predetermined threshold value.

If an amount of change in the index, e.g., the standard-deviation. SD of the index is equal to or smaller than a predetermined threshold value, it is possible to consider that the change in the index is relatively small. Therefore, this condition is set and employed to determine the referential period in which no heart abnormality exists.

According to another aspect of the present invention, the predetermined threshold value for the amount of change in the index is a value of mean(index)±1 SD.

This is one example for the predetermined threshold value for the amount of change in the index in the abnormality evaluation period. The threshold in an increasing direction may correspond to mean(index)+1 SD. The threshold in a decreasing direction may correspond to mean(index)−1 SD. The mean(index) is an average value of the index in the referential period. The 1 SD is a unit of the standard deviation of the index in the referential period.

According to another aspect of the present invention, the predetermined threshold value for the amount of change in the index is a variable according to the absolute value of the index in the referential period.

The index may be varied according to condition, such as age of an object human. Therefore, it is possible to evaluate the change in an index with sufficient accuracy by varying the threshold value of the change in the index in the abnormality evaluation period according to the absolute value of the index in the referential period.

According to another aspect of the present invention, the referential period is defined by using past data of the index.

The abnormality determination may be performed at the abnormality evaluation period just after the referential period. In such a case, it is possible to retrieve referential data from the referential period just before the abnormality evaluation period. Alternatively, the referential period may be set based on past data of the index. That is, the referential data for the abnormality determination may be retrieved from data in past period of time. For example, any period at least satisfies a predetermined condition may be employed as the referential period. The threshold value used for the determination of the change in the index may be determined based on an average value of the index observed during the referential period defined based on the data retrieved in the past time.

According to another aspect of the present invention, the abnormality determining means determines that the condition for the amount of change in the index is satisfied when the amount of change in the index in the abnormality evaluation period is within a range from mean(index)±1.5 SD to mean (index)±3.0 SD. This example shows how much amount of change in the index in the abnormality evaluation period is necessary to determine the abnormality based on the change in the index.

According to another aspect of the present invention, the abnormality determining means performs the determination based on a gradient of a regression line of the index during the abnormality evaluation period. Since a gradient of a regression line shows a rate of change in the index, it is possible to determine an abnormality based on the gradient of the regression line.

According to another aspect of the present invention, the determination using the gradient of the regression line is performed based on a threshold value that is variable according to the absolute value of the index during the referential period. As described above, the index may vary according to condition, such as age, of the object human. Therefore, it is possible to evaluate the change in the index with sufficient accuracy by varying the threshold value for determining the gradient of the regression line of the index in the abnormality evaluation period according to the absolute value of the index in the referential period.

According to another aspect of the present invention, the abnormality determining means changes an abnormal grade showing grade of the abnormality according to grade of the gradient of the regression line. It is considered that the gradient of the regression line changes according to a grade of an abnormality. Therefore, it is possible to indicate and reflect a grade of abnormality, a grade of danger, according to the gradient of the regression line.

According to another aspect of the present invention, in a case that the apparatus uses both the first and second indexes, the apparatus determines a final result of the determination when it is determined that both the indexes indicate the abnormality respectively. For example, the first index is indicative of the sympathetic nerve activity. The second index is indicative of the parasympathetic nerve activity. The abnormality determination may be performed with one of the first and second indexes. However, it is possible to improve accuracy of the abnormality determination by using both the first and second indexes.

According to another aspect of the present invention, in a case that the apparatus uses both the first and second indexes, the apparatus determines the symptom of the heart abnormality based on both of the indexes respectively. In addition, the apparatus determines an abnormal pattern which is used for the determination by adding a condition where the first index and the second index change in opposite increasing and decreasing directions. As shown in FIGS. 3A and 3B, and FIGS. 5A and 5B, if there is a symptom of a heart abnormality, the first index and the second index may change in opposite increasing and decreasing directions. Therefore, by using such a changing condition, the abnormal pattern can be determined. The abnormality determination can be performed with sufficient accuracy.

According to another aspect of the present invention, even if the apparatus, determines that the index indicates a symptom, the apparatus avoids determining the symptom when it is determined that the object human is in a time of beginning sleep, a time of amid sleep, or a time of getting up. When the object human is in a time of beginning sleep, a time of amid sleep, or a time of getting up, some disturbances resulting from actions of the object human may prevent a proper abnormality determination. Therefore, if the apparatus determines an abnormality, i.e., a symptom, in such a sleep relating period of time, the apparatus further determines that the determined abnormality is not adopted i.e., used, as a final result of the determination process.

According to another aspect of the present invention, the apparatus is able to be mounted on a vehicle. That is, the apparatus may be a vehicular apparatus. This example shows one of practical embodiments of the biological condition evaluation apparatus.

According to another aspect of the present invention, the determination is carried out when the vehicle is driven. In this configuration, it is possible to determine an abnormality of an abject human on the vehicle during driving the vehicle.

According to another aspect of the present invention, the apparatus further comprise at least one of a sensor which detects biological condition, an output device which outputs an announcement corresponding to the result of the determination, and a control device which performs control according to the result of the determination. In this configuration, it is possible to determine an abnormality based on a biological condition signal, such as an ECG signal, and a pulse signal, obtained by the sensor. In addition, if an abnormality is determined, it is possible to, announce information relating to the abnormality determination result, or to perform control according to the abnormality determination result.

According to another aspect of the present invention, the output device performs, in response to the determination of the symptom, at least one output among an announcement output asking subjective symptoms, an announcement output suggesting an electrocardiograph measurement, and an announcement output suggesting a blood-pressure measurement. It is possible to improve usefulness of the biological condition evaluation apparatus.

According to another aspect of the present invention, the output device performs, in response to the determination of the symptom, at least one output among an announcement output suggesting other abnormality determination different from one that is used in the determination, and an announcement output suggesting other biological measurement different from one that is used in the determination It is possible to improve usefulness of the biological condition evaluation apparatus.

According to another aspect of the present invention, the sensor performs, in response to the determination of the symptom, at least one measurement among an electrocardiograph measurement, and a blood-pressure measurement. It is possible to improve usefulness of the biological condition evaluation apparatus.

According to another aspect of the present invention, the present invention may take a form of a method comprising steps of calculating at least one of a first index and a second index by performing the frequency analysis on at least one of a heartbeat interval and a pulse interval, the first index being indicative of the sympathetic nerve activity, and the second index being indicative of the parasympathetic nerve activity; determining whether it is in a referential period which is a time period in which the index satisfies a predetermined condition which shows that a grade of change in the index calculated in the index calculating means is smaller than a predetermined value over a predetermined period; and determining a symptom of a heart abnormality after the predetermined condition is satisfied, the symptom being determined when the following both conditions (1) and (2) are satisfied during an abnormality evaluation period which is set after the referential period, (1) an amount of change in the index in an increasing and decreasing is equal to or greater than a predetermined threshold value which indicates that the amount of change is greater than an amount of change in the index observed during the referential period, and (2) a rate of change in the index in an increasing and decreasing is equal to or greater than a predetermined threshold value. According to another aspect of the present invention, the index calculating step calculates both the first and second indexes, the referential period determining step determines whether the both indexes indicate that it is the referential period, and the abnormality determining step determines the symptom of the heart abnormality with respect to both the indexes. According to another aspect of the present invention, the abnormality determining step discriminately determines whether both the indexes are in a first pattern in which changes in both the indexes indicate a symptom of a heart abnormality, a second pattern in which one of changes in both the indexes indicates a symptom of a heart abnormality, a third pattern in which changes in both the indexes indicate a symptom of a heart abnormality, and corresponds to opposite changes to the first pattern.

According to another aspect of the present invention, the present invention may be a form of program product stored in a computer readable storage medium, the computer program product comprising a computer program that, when executed on a computer, causes the computer to perform the method.

The computer readable storage medium is a tangible item, e.g., a flexible disk, a magneto-optical disk, CD-ROM, and a hard disk, etc. In addition, the computer readable storage medium may be a memory device, such as a ROM, a backup RAM, etc. The computer program recorded on one or more media may be loaded from the media to the computer and is run to cause the computer to perform the method, and to configure the computer as the apparatus described above.

BRIEF DESCRIPTION OF THE DRAWINGS

Additional objects and advantages of the present invention will be more readily apparent from the following detailed description of preferred embodiments when taken together with the accompanying drawings. In which.

DETAILED DESCRIPTION OF THE PREFERRED EMBODIMENTS

Hereinafter, embodiments of the present invention are described in detail referring to the attached drawings.

First Embodiment

In the first embodiment, a driver condition evaluation apparatus which evaluates a biological condition of a driver on a vehicle is explained as an example of an apparatus for evaluating biological condition.

Figure 1:
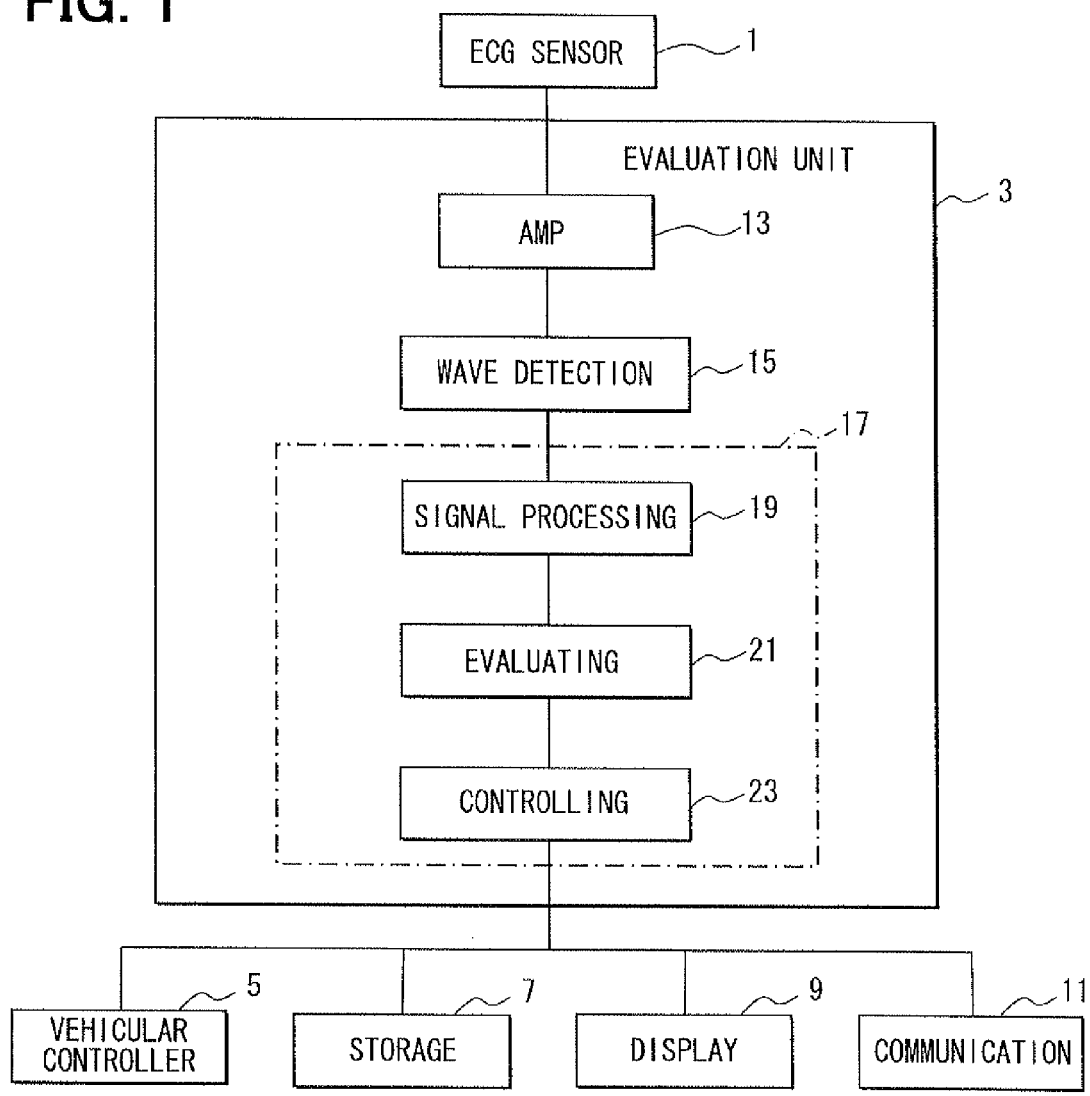
FIG. 1 is a block diagram showing a driver biological condition evaluation apparatus according to a first embodiment of the present invention.
Figure 2:
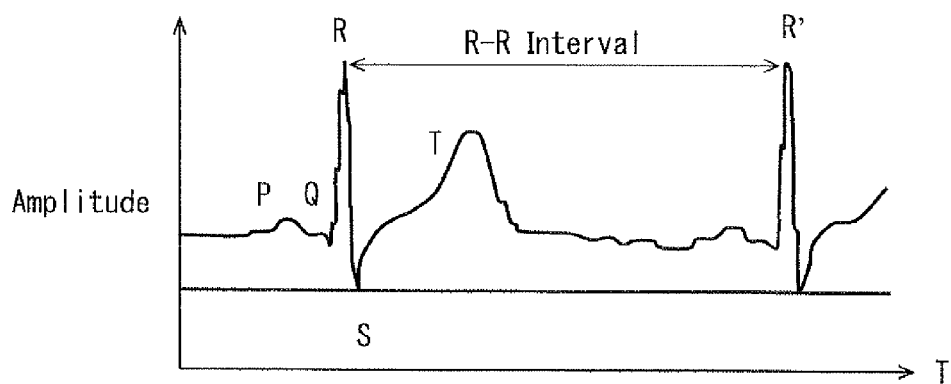
FIG. 2 is a graph showing an electrocardiogram obtained by an electrocardiograph sensor.

First, a basic configuration of the driver condition evaluation apparatus is explained based on FIG. 1 and FIG. 2.

As shown in FIG. 1, the driver condition evaluation apparatus is a system which is capable of determining or detecting that a driver is in an inappropriate condition for driving where the driver is advised not driving or should avoid driving due to the driver's health condition. In the embodiments, the inappropriate condition for driving is a condition where a symptom of a heart abnormality appears. The driver condition evaluation apparatus includes an ECG sensor 1, an evaluation unit 3 and several peripheral devices. The ECG sensor 1 is attached on a body of a driver on the vehicle and detects and measures a heart potential level. The evaluation unit 3 performs various kinds of operations based on the measured data of the ECG sensor 1, and determines biological condition of the driver. The peripheral devices include a vehicular controller 5, a storage device 7, a display 9 and a communication device 11. The vehicular controller 5 outputs a signal for controlling the vehicle based on the information from the evaluation unit 3. The storage device 7 memorizes various kinds of data, and is provided as a computer readable medium. The storage device 7 is recorded with computer program which causes a microcomputer to function as the driver condition evaluation apparatus. The display 9 is capable of displaying announcing information to the driver. The communication device 11 performs provides wireless communication with an external device.

Components are explained below. The evaluation unit 3 is an electronic control unit. The evaluation unit 3 includes an amplifier 13 which amplifies the signal from the ECG sensor 1, a wave detector 15 which detects data indicative of waveform of the ECG, and a microcomputer 17. The waveform detector 15 is provided with an analog-digital converter which transforms the analog signal from the ECG amplifier 13 into a digital signal to detect amplitude of the ECG signal. The microcomputer 17 performs various kinds of operations based on the signal from the waveform detector 15.

The microcomputer 17, as mentioned later, includes several sections functionally. The microcomputer 17 includes a signal processing section 19 which performs processing, such as a frequency analysis, on the signal from the ECG sensor 1. The microcomputer 17 includes an evaluating section 21 which evaluates biological condition of the driver and determines condition of the driver by using the processed result of the signal processing section 19. The microcomputer 17 includes a controlling section 23 which outputs signals to the peripheral devices to perform various kinds of vehicular control based on the result of the evaluating section 21.

The ECG sensor 1 may include a pair of electrodes for measuring cardiac potential of the driver and a main circuit part. The electrodes may be integrally installed in a steering wheel where the driver put hands. The main circuit part may be integrally installed inside the steering wheel. The ECG sensor 1 may be a seat type sensor which includes electrodes embedded in a seat where the driver sits down.

The electrocardiogram obtained by the ECG sensor 1 is explained. As shown in FIG. 2, the electrocardiogram includes several characteristic waveforms. For example, the P wave mainly reflects an electric excitation of an atrium. The Q, R and S waves reflect an electric excitation of a ventricle. The T wave reflects a repolarization process of an excited cardiac muscle cell in a ventricle. A group of the Q, R and S waves may also be referred to as a QRS complex. Among these, the R wave has the highest wave height, i.e., electric potential difference. It can be said that the R wave is the strongest against noises, such as electrical potential generated by muscle. The T wave has second high wave height. The P wave has the smallest wave height.

The R wave in the electrocardiogram may be detected by using a method in which the greatest peak detected from the original electrocardiogram or a differential waveform is determined as the R wave. Alternatively, the R wave may be detected by using a method, disclosed in JP2007-301101A which uses a template to detect the R wave.

In the electrocardiogram, an interval between a leading peak of the R wave and a trailing peak of the R wave is referred to as the heartbeat interval RRI. The heart rate can be calculated by multiplying 60 to the reciprocal of the heartbeat interval RRI.

A variation of the heartbeat interval RRI is referred to as a heartbeat interval variation HRV. A biological condition of an object human can be evaluated and determined based on the heartbeat interval variation HRV. It is said that an amount of autonomic nerve activities can be evaluated and determined by conducting a frequency analysis on the heartbeat interval which can be considered as an index indicative of the heartbeat interval variation HRV. For example, the Fast Fourier Transform can be used as a method of the frequency analysis. In detail, a high frequency component HF and a low frequency component LF of the data are used in the embodiment. The components HF and LF are obtained by conducting the frequency analysis on the heartbeat interval. It is said that an amount of the parasympathetic nerve activity is reflected on the HF. It is also said that an amount of the sympathetic nerve activity is reflected on a ratio LF/HF. For example, the high frequency component HF has 0.15-0.4 Hz in frequency. For example, the low frequency component LF has 0.04-0.15 Hz in frequency. Hereinafter, the components HF and LF, and the ratio LF/HF may be referenced by the symbols HF, LF, and LF/HF respectively. Similarly, the heartbeat interval RRI may be referenced by the symbol RRI. The heart rate HR may be referenced by the symbol HR. The heartbeat interval variation HRV may be referenced by the symbol HRV.

Returning to FIG. 1, the signal processing section 19 calculates at least one index indicative of the heartbeat interval variation based on the waveform of the electrocardiogram acquired in the waveform detector 15. The signal processing section 19 calculates at least one of RRI, HR, HF, and LF/HF.

The evaluating section 21 estimates a biological condition of a driver based on a time-based variation, i.e., a time-based change, of the index which shows the heartbeat interval variation HRV, such as RRI, HR, HF, and LF/HF, obtained by the signal processing section 19. The condition of the driver corresponds to a capability of proper driving of the vehicle. The condition is provided by discriminating and determining whether the driver is in an appropriate condition for driving or in an inappropriate condition for driving. Here, the inappropriate condition for driving is a condition in which a symptom of a heart abnormality appears before an actual heart abnormality appears. Therefore, the inappropriate condition for driving is not a condition in which the actual heart abnormality has been appeared.

The controlling section 23 determines what kind of action shall be caused to the driver, a passenger, or a vehicle, etc. based on the determination result of the evaluating section 21, and outputs the signal according to the determination to the vehicular controller 5, the storage device 7, the display device 9 and the communication device 11.

When the determination result of the evaluating section 21 indicates that the driver is in the inappropriate condition for driving, the controlling section 23 instructs the vehicular controller 5 to perform at least one protective measure for the driver, a passenger, a vehicle, or other vehicle on the traffic. For example, the protective measure includes a drive support operation. For example, the vehicular controller 5 may automatically operate a brake device to apply braking force to the vehicle gradually, and even to stop the vehicle. The vehicular controller 5 may turn on a hazard lamp to be blinked in order to give cautions to the other vehicles on the traffic. The vehicular controller 5 may include a sensor which performs the protective measure. The protective measure includes at least one measurement among an electrocardiograph measurement, a blood-pressure measurement, and other biological measurement different from one that is used in a heart abnormality determination in this embodiment. The vehicular controller 5 may include an output device which performs the protective measure. The protective measure includes at least one output among an announcement output suggesting other abnormality determination different from one that is used in the determination, an announcement output asking subjective symptoms, an announcement output suggesting an electrocardiograph measurement, an announcement output suggesting a blood-pressure measurement and an announcement output suggesting other biological measurement different from one that is used in the determination.

The storage device 7 stores data necessary for the apparatus. The storage device 7 may be a storage medium storing a computer program for the apparatus. The storage device 7 stores data when the controlling section 23 determines that data storage is necessary. The stored data may be used for a diagnosis purpose. For example, the storage device 7 stores at least one of the electrocardiogram, RRI, HR, HF, LF/HF, and the determination result of the driver's biological condition.

The display device 9 is a vehicular display device, such as a liquid crystal display, and an organic electroluminescence display. The display device 9 displays the heart rate HR (reciprocal of the heartbeat interval RRI multiplied by 60), the heartbeat interval variation HRV, and the determination result of the driver's biological condition. The display device 9 may be provided by a display on a navigation apparatus.

The communication device 11 is a device for performing communication with external devices and networks. The communication device 11 may also performs at least one protective measure in response to an instruction from the controlling section 23. The protective measure may include making a call or warning to predetermined contacts, such as a medical institution and an emergency, and making a data communication to transmit positioning information of the vehicle in order to help other person to locate the vehicle. The display device 9 and the communication device 11 may be an output device to perform the protective measure in response to the determination of the symptom of the heart abnormality.

Next, a method for determining at least the inappropriate condition for driving based on the data obtained from the ECG sensor 1 is explained in detail.

The method of identifying a plurality of abnormal patterns is used for this case of the operation. The embodiment uses an abnormal determination method of identifying a plurality of abnormal patterns which are characterized with waveforms. The embodiment uses three sorts of techniques depending on three abnormal patterns of waveforms of the electrocardiogram as shown in FIG. 3A-FIG. 5B. The abnormality determination in this embodiment is a determination of a symptom of a heart abnormality. Each drawing shows actual data before a heart is suffered with an actual abnormality. lnHF, and ln(LF/HF) show values of the natural logarithm of HF, and LF/HF respectively, which are explained later. In this embodiment, the data lnHF and in(LF/HF) are acquired and stored as time-based series data, and are processed. In the following explanation, a group of time-based series data is expressed as T(lnHF) and T(ln(LF/HF)). The variables HF, LF/HF, lnHF, ln(LF/HF), T(lnHF) and T(ln(LF/HF)) are the indexes in this embodiment. In the drawings, a monitoring period, a referential period, and a evaluation period are illustrated. The apparatus monitors the index at least for the monitoring period for performing the abnormal determination. The apparatus determines and gets a referential data, such as a threshold, based on data in the referential period. The apparatus evaluates the driver's biological condition and determines a symptom of a heart abnormality based on data in the evaluation period. The evaluation period is defined after the referential period.

First Abnormal-pattern

Figure 3A:
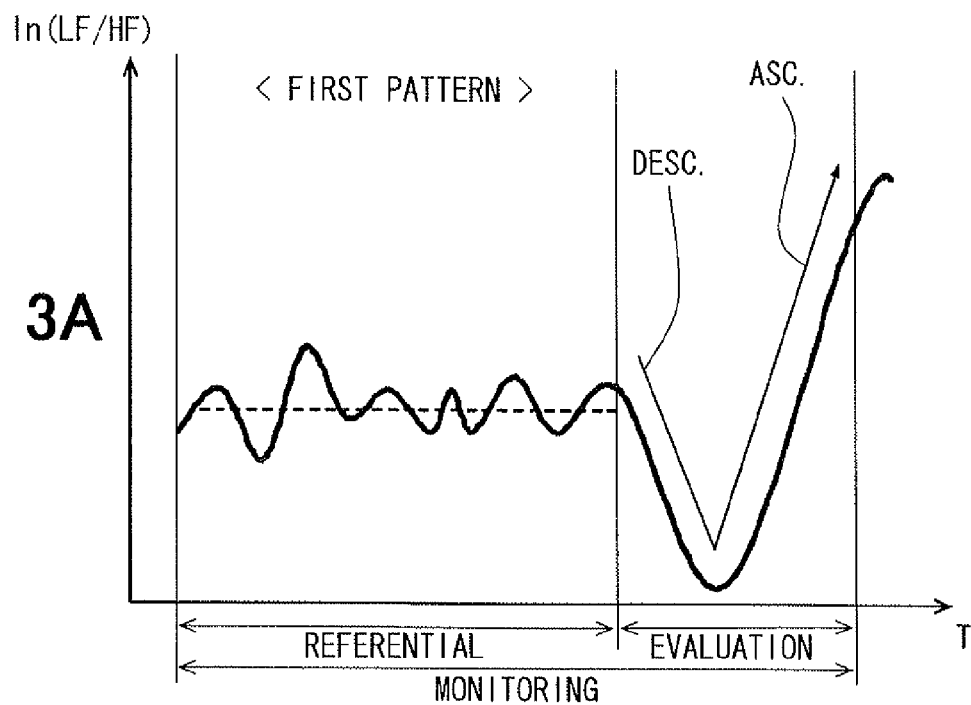
FIG. 3A is a graph showing a first abnormal-pattern.
Figure 3B:
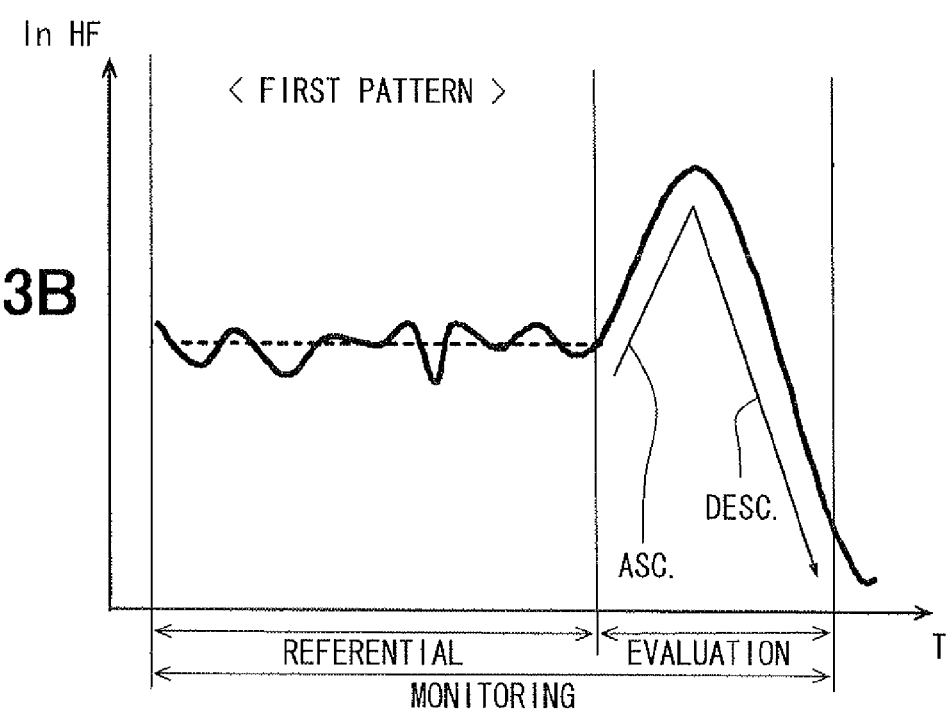
FIG. 3B is a graph showing the first abnormal-pattern.

FIG. 3A and FIG. 3B show a first abnormal-pattern. In the first abnormal-pattern, the indexes T(lnHF) and T(ln(LF/HF)) show a distinctive behavior in a period of time after the referential period. The period of time after the referential period is the evaluation period.

In the first abnormal-pattern, the index T(ln(LF/HF)) indicative of the sympathetic nerve activity decreases rapidly, and then, increases rapidly in the evaluation period, as shown in FIG. 3A. Simultaneously, the index T(lnHF) indicative of the parasympathetic nerve activity increases rapidly, and then, decreases rapidly, as shown in FIG. 3B. In the drawings, a symbol "DESC," shows a descending phase of the index. A symbol "ASC." shows an ascending phase of the index. The indexes T(ln(LF/HF)) and T(lnHF) change in opposite increasing and decreasing directions, but, change correspondingly with each other. Both the indexes T(ln(LF/HF)) and T(lnHF) show distinctive behaviors.

One typical case of the inappropriate condition for driving can be detected by detecting and determining such a change of the indexes T(lnHF) and T(ln(LF/HF)) as shown in FIGS. 3A and 3B.

Second Abnormal-pattern

Figure 4A:
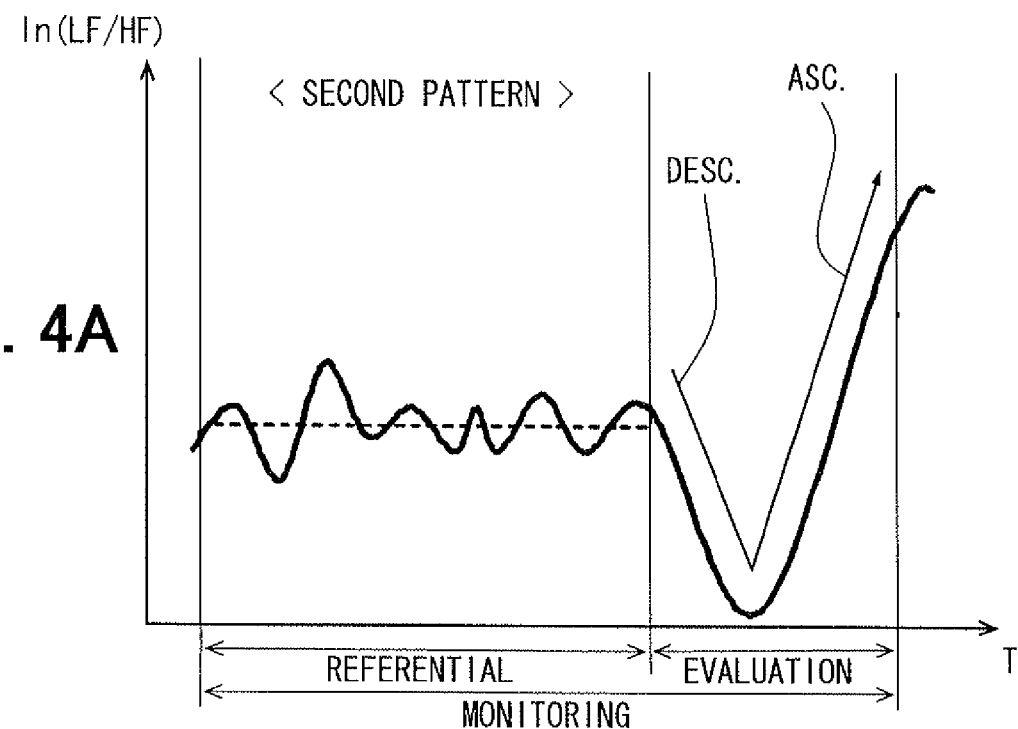
FIG. 4A is a graph showing a second abnormal-pattern.
Figure 4B:
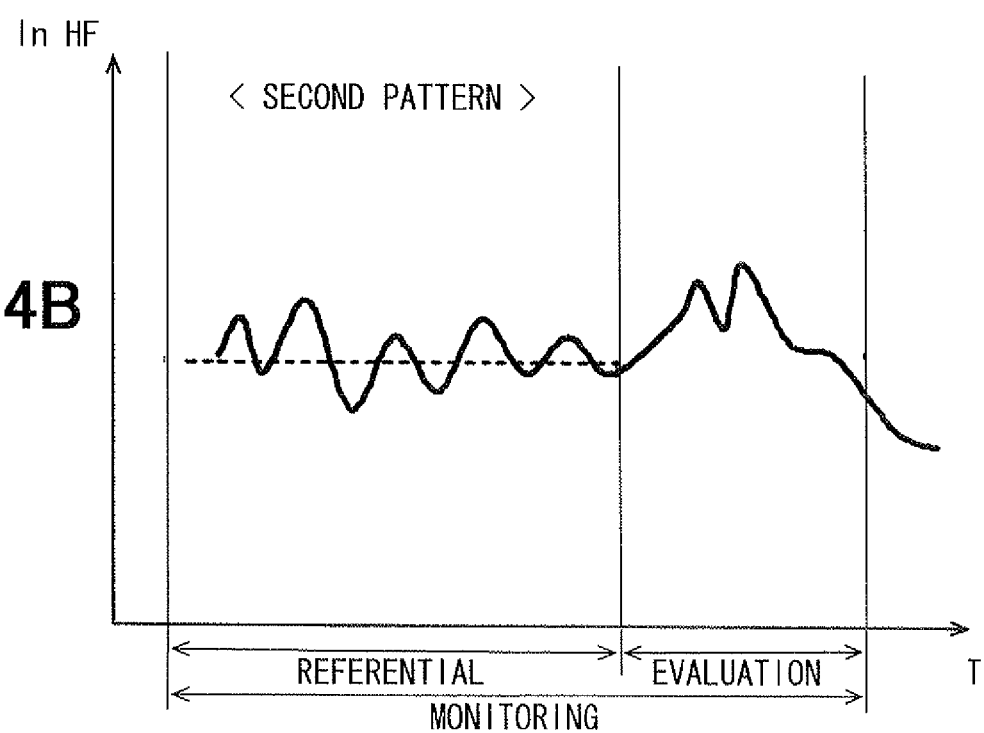
FIG. 4B is a graph showing the second abnormal-pattern.

FIG. 4A and FIG. 4B show a second abnormal-pattern. In the second abnormal-pattern, the indexes. T(lnHF) and T(ln (LF/HF)) show a distinctive behavior in the evaluation period.

In the second abnormal-pattern, the index T(ln(LF/HF)) indicative of the sympathetic nerve activity decreases rapidly, and then, increases rapidly in the evaluation period, as shown in FIG. 4A. On the other hand, the index T(lnHF) indicative of the parasympathetic nerve activity does not change decreasingly as shown in FIG. 4B. The index T(lnHF) fluctuates similar to that in the referential period. One of the indexes T(ln(LF/HF)) and T(lnHF) shows a distinctive behavior, but the other one shows an indistinctive behavior and changes differently from the distinctive one.

One typical case of the inappropriate condition for driving can be detected by detecting and determining such a change of the indexes T(lnHF) and T(ln(LF/HF)) as shown in FIGS. 4A and 4B.

Third Abnormal-pattern

Figure 5A:
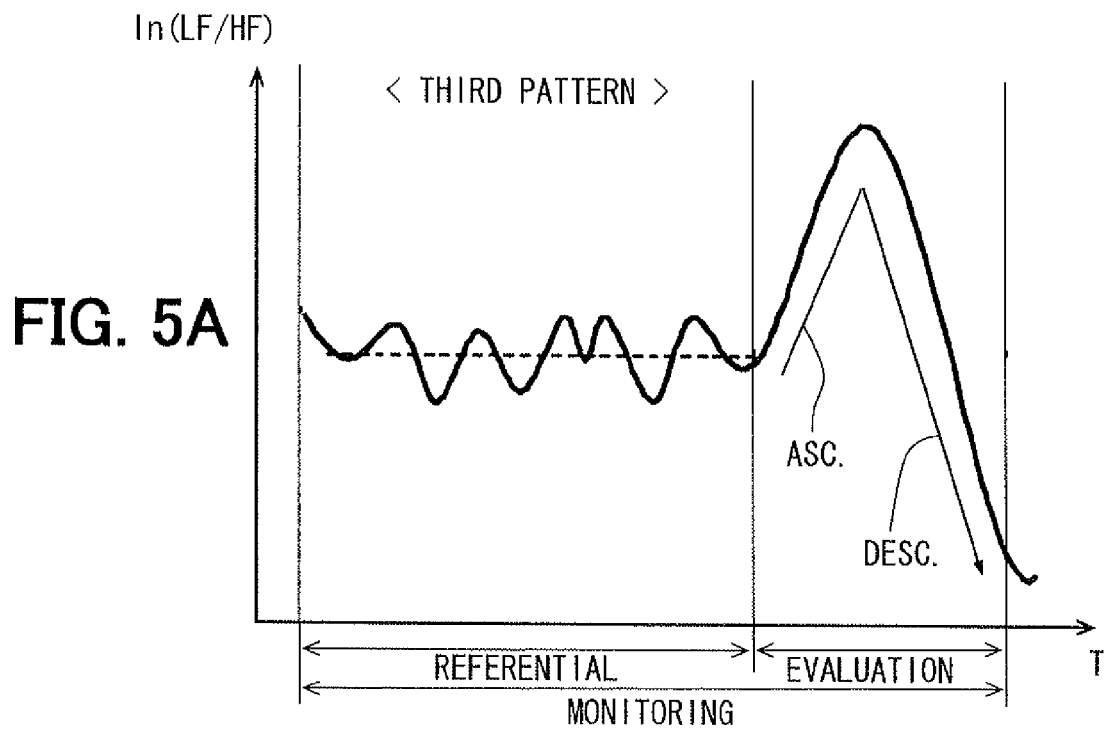
FIG. 5A is a graph showing a third abnormal-pattern.
Figure 5B:
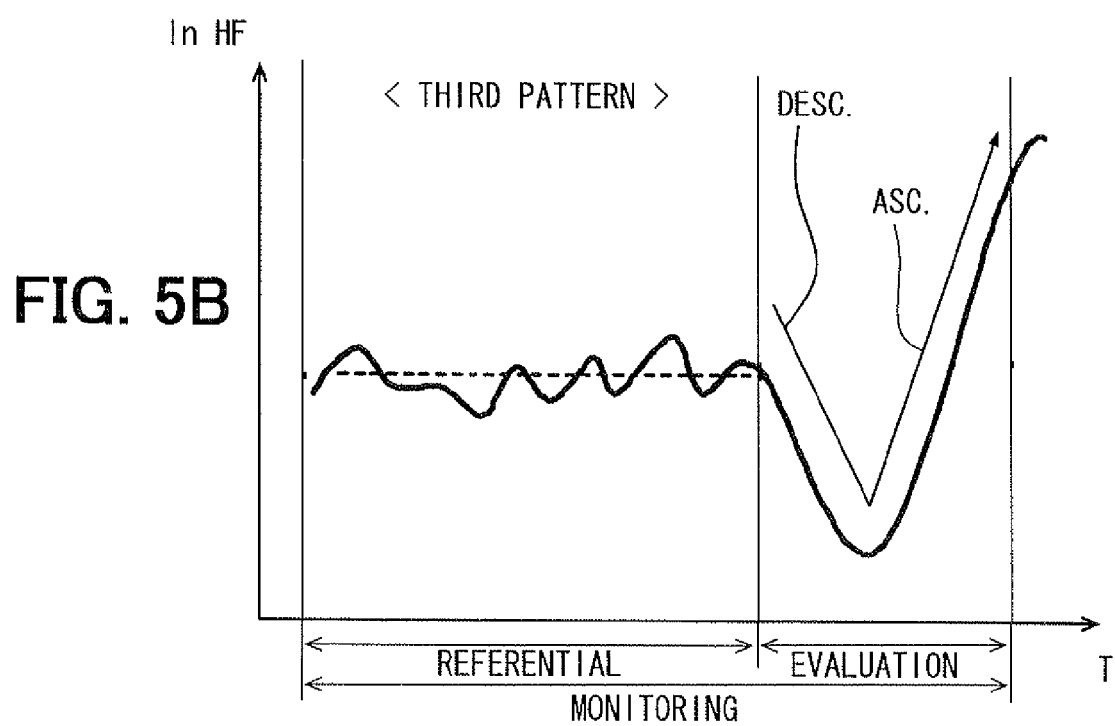
FIG. 5B is a graph showing the third abnormal-pattern.

FIG. 5A and FIG. 5B show a third abnormal-pattern. In the third abnormal-pattern, the indexes T(lnHF) and T(ln(LF/HF)) show a distinctive behavior in the evaluation period.

In the third abnormal-pattern, the index T(ln(LF/HF)) indicative of the sympathetic nerve activity increases rapidly, and then, decreases rapidly in the evaluation period, as shown in FIG. 5A. Simultaneously, the index T(lnHF) indicative of the parasympathetic nerve activity decreases rapidly, and then, increases rapidly, as shown in FIG. 5B. The indexes T(ln(LF/HF)) and T(lnHF) change in opposite increasing and decreasing directions, but, change correspondingly with each other. Both the indexes T(ln(LF/HF)) and T(lnHF) show distinctive behaviors. The indexes T(lnHF) and T(ln(LF/HF)) in the third abnormal-pattern show opposite behavior to the first abnormal-pattern. In other words, the indexes in the third abnormal-pattern change in opposite increasing and decreasing directions with respect to the indexes in the first abnormal-pattern.

One typical case of the inappropriate condition for driving can be detected by detecting and determining such a change of the indexes T(lnHF) and T(ln(LF/HF)) as shown in FIGS. 5A and 5B.

Thus, the inappropriate condition for driving can be determined based on the abnormal patterns. In the first and third abnormal-patterns, the inappropriate condition for driving can be determined based on both the indexes T(lnHF) and T(ln(LF/HF)). In the second abnormal-pattern, the inappropriate condition for driving can be determined based on the index T(ln(LF/HF)) only. Both the indexes behave in distinctive changes in, the first and third abnormal-patterns. Therefore, if those patterns are determined, it is possible to determine that there may be a higher risk of actual heart abnormalities than the second abnormal-pattern. That is, a determination of the first and third abnormal-patterns shows a higher possibility of suffering from actual heart abnormalities than that in a determination of the second abnormal-pattern.

Condition for the Referential Period

Here, the referential period used in the determination of the first or third abnormal-patterns is explained. In the embodiment, the referential period is a fixed period of 120 minutes. The evaluation period is a fixed period of 60 minutes.

Figure 6:
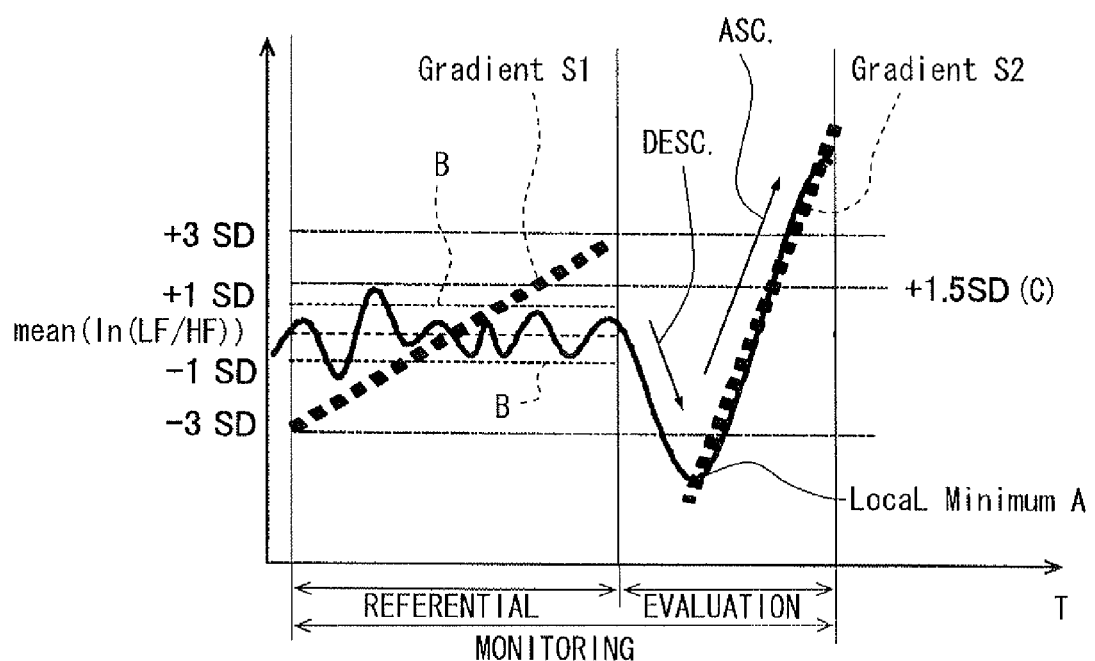
FIG. 6 is a graph showing a gradient of a regression line of In(LF/HF)

As shown in FIG. 6, in the referential period, at least one of the indexes is required to have an amount of change that is smaller than a certain range. In this embodiment, if an out-of-range ratio of T(ln(LF/HF)) is continuously smaller than a predetermined threshold over 120 minutes, the apparatus determines that the period of 120 minutes is appropriate for the referential period and employs and stores data observed during the period of 120 minutes as the data in the referential period. The out-of-range ratio indicates a ratio of time in which the value of ln(LF/HF) is out of a range defined by an expression mean(index)±1 SD, where mean(index) is an average value of T(ln(LF/HF)) for the time of 120 minutes, and 1 SD is a unit of the standard deviation of T(ln(LF/HF)) for the time of 120 minutes.

The condition for determining the referential period may be referred to as a first condition "X" for determining whether the data is appropriate as the data in the referential period or not. The first condition "X" may be also referred to as a referential period data evaluating condition. The first condition may be replaced with other mathematical condition which shows that a grade of change in the index is smaller than a predetermined value over a predetermined period.

It is known that an absolute values of the index, such as T(lnHF) and T(ln(LF/HF)), includes components reflecting individual differences. For example, it is known that an absolute value of the index becomes small as a heart function declines. For example, it is also known that an absolute value of the index, such as LF and LF/HF, becomes weak as an age increases.

In order to improve the abnormality determination by reflecting such a steady shift of the index, the apparatus uses variables for the threshold values. The predetermined threshold values are set so that the abnormality determination shows a tendency in which an abnormality is determined more easily as the absolute value decreases. The predetermined threshold values are set so that the apparatus determines an abnormality more hardly when an absolute value of the index is relatively great, and determines an abnormality more easily when an absolute value of the index is relatively small.

In detail, the threshold value is set at ¼ of whole length of a provisional referential period, if at least one of conditions "mean(In(LF/HF))±1 SD is equal to or greater than 1.5" and "the maximum of T(In(LF/HF)) is equal to or greater than 1.5" is satisfied. The whole length of the provisional referential period is 120 minutes. In this case, the apparatus calculates a total time in which In(LF/HF) is out of a range defined by mean(In(LF/HF))±1 SD in the provisional referential period, i.e., 120 minutes. If the total time is shorter than the ¼ of 120 minutes, the apparatus determines that it is appropriate as the referential period.

Mean(In(LF/HF)) is an average value of T(In(LF/HF)). Mean(In(LF/HF))±1 SD shows levels "B" illustrated in FIG. 6.

On the other hand, the threshold value is set at ⅓ of whole length of a provisional referential period, if at least one of conditions "mean(In(LF/HF))±1 SD is equal to or greater than 1.5" and "the maximum of T(In(LF/HF)) is equal to or greater than 1.5" is not satisfied. If the total time is shorter than the ⅓ of 120 minutes, the apparatus determines that it is appropriate as the referential period.

As a result, the condition for the abnormality determination is loosened and is set to determine an abnormality easily as an absolute value of the index T(In(LF/HF)) becomes smaller. In other wards, the settings of threshold value makes easy to determine a heart abnormality.

As explained above, the referential period can be determined by using a determining method based on a behavior of the index T(In(LF/HF)).

The referential period can be determined based on the index T(InHF) by using the same determining method. The apparatus performs the same determining method on the index T(InHF). The method based on the T(InHF) is understandable from the above explanation, therefore an explanation is omitted.

The data observed and retrieved during the referential period is considered and used as a referential data in a data base for defining a normal condition. Therefore, it is not necessary to observe and retrieve data in the predetermined referential period for every time of the abnormality determination. For example, a determination for the referential period, i.e., a determination for beginning of the evaluation period, can be performed by using measured and stored data in the past operation. In this case, it is possible to eliminate a measuring time for the referential period. The threshold value for determining the referential period may be referred to as a stability threshold.

Condition for the Evaluation Period

Next, the abnormality determination performed based on changes in the indexes during the evaluation period following the referential period is explained.

In this embodiment, the apparatus detects a local minimum point or a local maximum point in the predetermined evaluation period. The local minimum point and the local maximum point may be defined as a minimum point and a maximum point that exceeds a predetermined range, such as mean (In(LF/HF))±3 SD. Detecting the local minimum point and the local maximum point provides a condition which shows that an amount of change in the index in an increasing and decreasing is equal to or greater than a predetermined threshold value. The predetermined threshold value indicates that the amount of change is greater than an amount of change in the index observed during the referential period. The threshold value for determining amplitude of change in the index in the evaluation period may be referred to as an amplitude threshold. Then, the apparatus determines whether the index changes rapidly after the referential period. In detail, the apparatus determines whether the index changes rapidly in an increasing direction or in a decreasing direction after the referential period. Detecting a rapid change of the index provides a condition which shows that a rate of change in the index in an increasing and decreasing is equal to or greater than a predetermined threshold value. The threshold value for determining a speed of change in the index in the evaluation period may be referred to as a speed threshold.

For example, the local minimum point "A" appearing just after the referential period can be detected by using a condition, such as "A is equal to or smaller than mean(In(LF/HF))−3 SD." Similarly, the local maximum point "A" appearing just after the referential period can be detected by using a condition, such as "A is equal to or greater than mean(In(LF/HF))+3 SD." The value of mean(In(LF/HF)) may be obtained based on data retrieved during the referential period. The value of SD, which is the standard deviation of the index, may be obtained based on data retrieved during the referential period. The value 3 SD, which defines the threshold value, may be replaced with a value within a range from 2 SD to 3 SD, or a range from 1.5 SD to 3.0 SD.

Referring to FIG. 6, the data plotted on the graph show a decreasing change after the referential period. Therefore, in this case, the local minimum point "A" is detected.

The condition for determining an amount of change in the index in the evaluation period may be referred to as a second condition "Y" for determining whether the data shows a significant change in the evaluation period or not. The second condition "Y" may be also referred to as an amplitude determining condition.

However, the amount of change alone is insufficient to determine a rate of changing in increasing or decreasing directions. Therefore, in actual processing, the second condition "Y" includes an additional condition which shows that the local minimum point or the local maximum point is detected before elapsed a half of the evaluation period, i.e., 30 minutes. The apparatus determines that the condition "Y" is satisfied only when the point "A" is detected within 30 minutes after the referential period is completed.

Next, in a case that the point "A" is the local minimum point, the apparatus determines whether the index rapidly increases from the local minimum point or not. On the contrary, in a case that the point "A" is the local maximum point, the apparatus determines whether the index rapidly decreases from the local maximum point or not.

Here, detecting a rapid change of the index is performed based on a gradient of a regression line of the index after the local minimum point or the local maximum point. The regression line may be determined based on the data of the index after elapsed a predetermined time from the local minimum point or the local maximum point. The regression line may be determined based on the data of the index from the local minimum point or the local maximum point to the end of the evaluation period.

The condition for determining a rapid change in the index in the evaluation period may be referred to as a third condition "Z" for determining whether the data shows a significant change in the evaluation period or not. The third condition "Z" may be also referred to as a gradient determining condition.

However, the gradient of the regression line alone is insufficient to determine an amount of change in the index from the local minimum point or the local maximum point in increasing or decreasing directions. Therefore, in actual processing, the third condition "Y" includes an additional condition which reflects the amount of change in the index in the evaluation period to the determination in the third condition "Y". For example, the apparatus calculates an amount of change in the index in the evaluation period, such as an amount of change from the local minimum point or the local maximum point, or an amount of change from a predetermined level, such as mean(ln(LF/HF)). The apparatus determines that the condition "Z" is satisfied only when the calculated amount of change in the index in the evaluation period is equal to or greater than a predetermined threshold value.

Referring to FIG. 6, an example in which the index increases from the local minimum point is explained. An example in which the index decreases from the local maximum point can be understood by inversing positive/negative in the following explanation.

As shown in FIG. 6, the apparatus calculates a gradient S1 of a line which is a straight line from mean(ln(LF/HF))−3 SD at a beginning of the referential period to mean(ln(LF/HF))+3 SD at an end of the referential period.

On the other hand, the apparatus calculates a gradient S2 of a regression line of T(ln(LF/HF)) from the local minimum point "A" to the end of the evaluation period.

Then, the apparatus performs the abnormality determination by comparing the gradient S2 of the regression line with the gradient S1 which represents an amount of change in the index in the referential period. Predetermined threshold values in the abnormality determination processing are variables and are set in a similar manner to the stability determination for the referential period. The predetermined threshold values are set to loosen the condition and to detect an abnormality more easily as an absolute value of the index T(ln(LF/HF)) becomes small.

In detail, the third condition "Z" can be divided into three expressions shown below. In the expressions, "C" is a value of mean(ln(LF/HF))+1.5 SD calculated based on the data in the referential period. The following expressions are defined based on data obtained from 31 actual patients.

1. First Expression
When C<0, $$S2 > S1 \times \text{Exp}(C-0.5)$$

2. Second Expression
When 1>C≥0, $$S2 > S1 \times (C + \text{Exp}(-0.5))$$

3. Third Expression
When C≥1, $$S2 > S1 \times \text{Exp}(C)$$

Then, in each of the cases, if the expression is satisfied, the apparatus determines that the index indicates a heart abnormality, i.e., a symptom of the heart abnormality. If the value C is smaller than 0, the apparatus uses the first expression to determine an abnormality. If the value C is equal to or greater than 0 and the value C is smaller than 1, the apparatus uses the second expression to determine an abnormality. If the value C is equal to or greater than 1, the apparatus uses the third expression to determine an abnormality. In the expressions, the right-side is used as a threshold which becomes greater as the value "C" increases. Therefore, the abnormality can be determined in a smaller gradient when the value C, which represents an absolute value, is small. Contrary, when the value C is relatively great, it is necessary to be observed a relatively greater gradient to determine the abnormality.

As explained above, a heart abnormality can be determined by using a determining method based on a behavior of the index T(ln(LF/HF)) in the evaluation period. A heart abnormality can be determined based on the index T(lnHF) by using the same determining method. The apparatus performs the same determining method on the index T(lnHF). The method based on the T(lnHF) is understandable from the above explanation, therefore an explanation is omitted.

Although the above explanation were made based on V-shape changes (from descending to ascending) of the index T(ln(LF/HF)) shown in FIG. 3A and FIG. 4A, a reverse V-shape change (from ascending to descending) of the index T(ln(LF/HF)) shown in FIG. 5A can also be evaluated by using a similar method to the above.

In this case, the apparatus detects a phase change from an ascending to a descending. Therefore, a gradient to be evaluated by the above mentioned method takes negative value. A heart abnormality is determined when the gradient takes relatively great negative value.

It is possible to perform an abnormality determination based on a reverse. V-shape change of the index T(lnHF) shown in FIG. 3B, and a V-shape change of the index T(lnHF) shown in FIG. 5B by using the same method explained above.

In addition to a method in which the threshold value is set to the gradient, the apparatus may include a section which classifies the determined abnormality into plurality of grades based on a ratio between the gradients S1 and S2. For example, the grade may correspond to a seriousness grade of the determined abnormality. The apparatus includes a section which calculates a ratio S2/S1, and the classifying section which gives a higher grade to the determined abnormality as the ratio becomes greater.

In addition, the apparatus may include a section which changes an action level of the protective measure according to the grade of the abnormality. The changing section may be included in the controlling section 23. For example, the apparatus may change contents of the warning message so that the apparatus strengthens the grade of warning as the grade of abnormality increases. The apparatus may shifts or modifies a control of the vehicle in a proper side as the grade of abnormality increases. The apparatus reduces a speed of vehicle according to the grade. The apparatus may increase a braking force according to the grade.

Next, processing performed by the microcomputer 17 in the evaluation unit 3 is explained. The processing, i.e. a program is designed based on the above explained principle.

Figure 7:
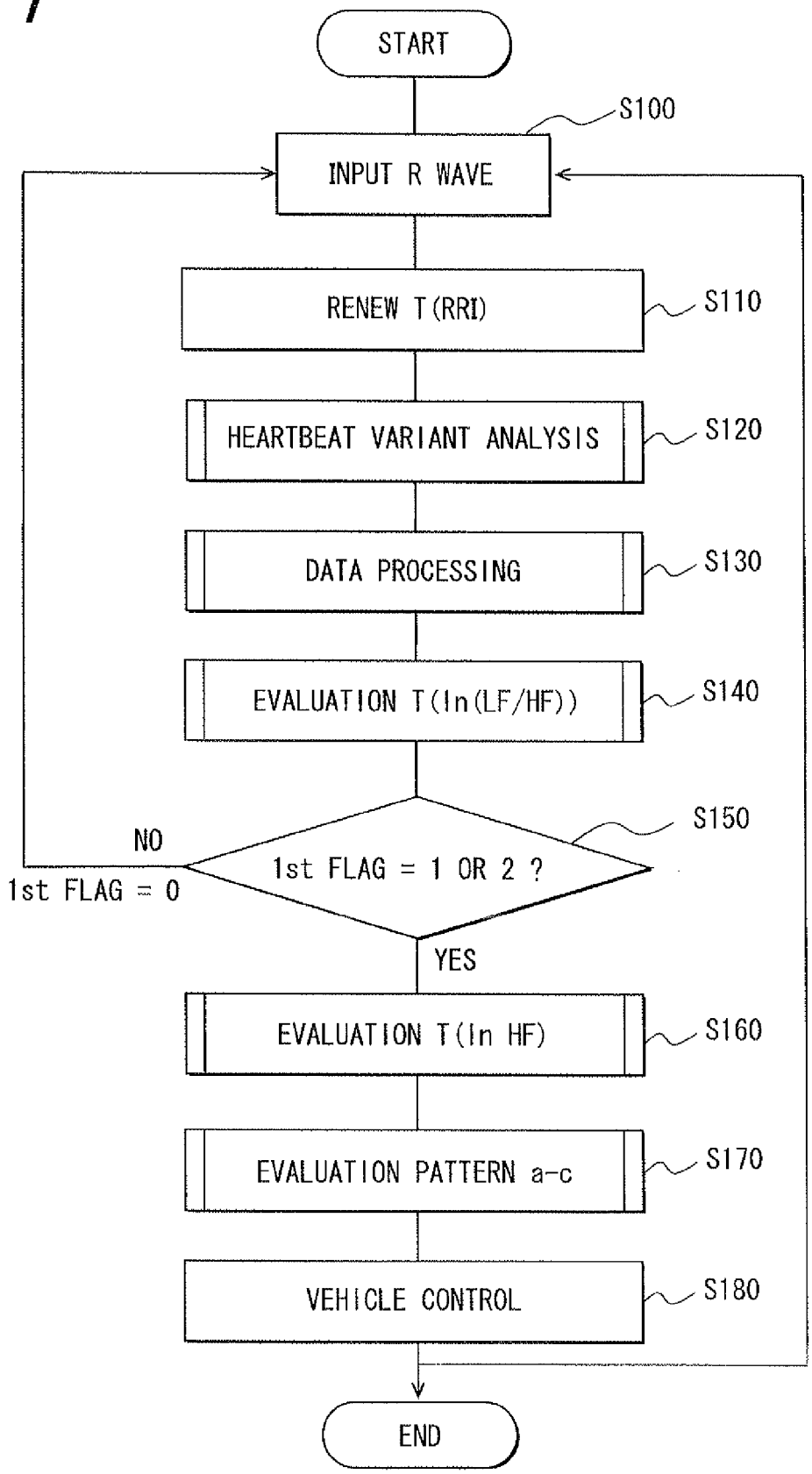
FIG. 7 is a flow chart showing a main routine for an abnormality determination processing according to the first embodiment of the present invention.

First, a main routine is explained. FIG. 7 shows a flow chart. In a step S100, the apparatus inputs an R wave based on the signal acquired from the waveform detector 15.

In a following step S110, the apparatus calculates the heartbeat interval RRI based on the inputted R wave, and renews, i.e., updates, the time-based series data of, the heartbeat interval RRI by memorizing the calculated RRI in a storing manner. This updating is performed at a timing of the abnormality determination. For example, it is performed every minute. Therefore, the time-based series data of the heartbeat interval RRI is updated periodically.

In a following step S120, a heartbeat-variation-analysis is performed. Detail is explained later. That is, the apparatus analyzes variations of the heartbeat interval RRI and calculates the newest time-based series data T(HF) and T(LF/HF).

In a following step S130, data processing is performed on T(HF), and T(LF/HF). Detail is explained later. That is, the apparatus calculates T(InHF) and T(In(LF/HF)) based on T(HF) and T(LF/HF), which are used for the abnormality Determination.

In a following step S140, the apparatus evaluates T(In(LF/HF)) to perform the abnormality determination. Detail is explained later. That is, the apparatus determines whether an abnormality exists or not based on T(In(LF/HF)). The existence of the abnormality corresponds to an inappropriate condition for driving. If the abnormality is determined, the apparatus sets a first flag which indicates at least an existence or non-existence of an abnormality. The first flag indicates at least an existence or non-existence of an abnormality. The first flag can take three values, where "0" shows the non-existence of the abnormality, "1" and "2" show the existence of the abnormality. The first condition may be referred to as a first index abnormal flag or a T(In(LF/HF)) abnormal flag.

In a following step. S140, it is determined that whether the first flag set based on T(In(LF/HF)) indicates "0", "1", or "2". If the first flag indicates "1" or "2", the apparatus proceeds to a step S160. On the other hand, if the first flag indicates "0", the apparatus returns to the step S100.

In a step S160, the apparatus evaluates T(InHF) to determine a heart abnormality. Detail is obtained later. That is, the apparatus performs a further abnormality determination based on T(InHF) in addition to the abnormality determination based on T(In(LF/HF)).

In a following step S170, the apparatus evaluates the indexes to determine the abnormal-pattern. Detail is explained later. That is, the apparatus determines that which one of the first to the third abnormal-patterns is most fit to a present waveform of the indexes.

In a following step S180, the apparatus performs an action, which is a control of the vehicle, based on the result of the abnormality determination. Detail is explained later. That is, the apparatus performs a protective measure by using the vehicular controller 5, the storage device 7, the display device 9, and the communication device 11. The apparatus may perform a plurality of protective measure in response to the abnormality. Then, the apparatus once completes processing.

Figure 8:
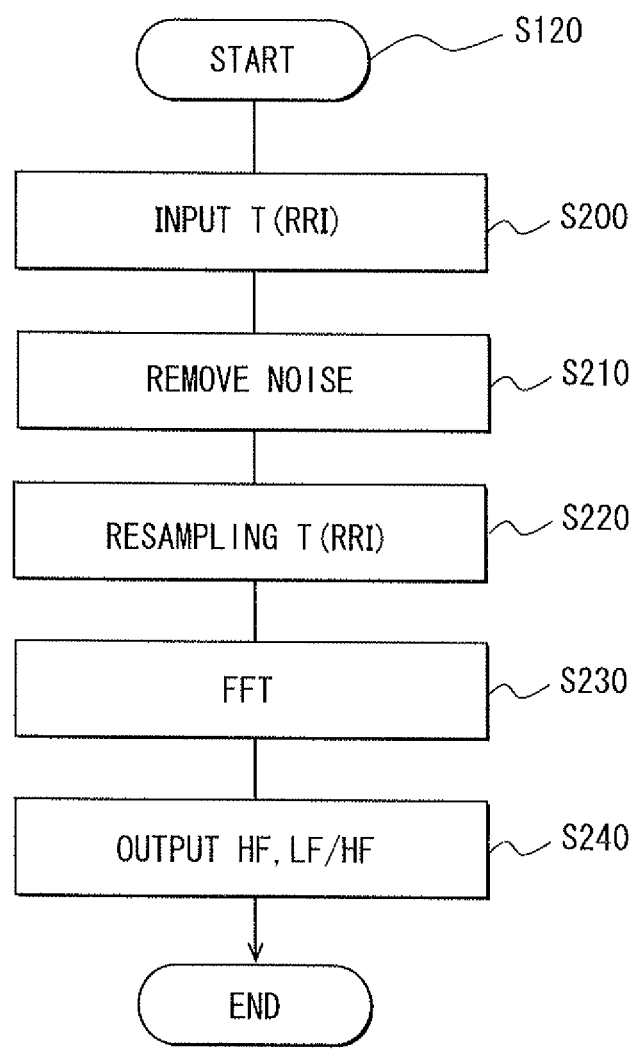
FIG. 8 is a flow chart showing a heartbeat variation analysis processing.

Referring to FIG. 8, the heartbeat-variation-analysis processing is explained in detail. The processing performs a frequency analysis on the heartbeat interval RRI. As shown in FIG. 8, in a step S200, the apparatus inputs T(RRI).

In a following step S210, the apparatus performs noise reduction processing on T(RRI). The noise which is superimposed on T(RRI) and is caused by a body motion of the driver, etc., is removed from T(RRI). For example, the noise reduction processing is performed by detecting whether a target RRI is distanced apart from a median of RRI for a total of ten beats located before and after the target RRI by more than the standard deviation of all the data, and removing the target RRI that is out of the standard deviation.

In a following step S220, the apparatus creates a new set of time-based series data of RRI by re-sampling T(RRI) inputted in the step S200. In detail, the apparatus performs well-known Berger algorithm.

In a following step S230, the apparatus performs a frequency analysis, to the data of T(RRI) obtained in the step S220, and calculates the newest HF and LF/HF based on a power of a predetermined frequency band. For example, the apparatus performs analysis using the Fast Fourier Transform.

An amplitude value of a power spectrum is an amount of a specific frequency component, i.e., the high frequency component HF, and the low-frequency component LF. It is possible to monitor an amount of change of respective components continuously, based on a change of the amplitude value along the time line. In addition, HF and LF can be obtained by integrating the components in the respective one of frequency bands. The amplitude value may also be referred to as a strength or a power.

In a following step S240, the apparatus stores and outputs HF and LF/HF calculated in the step S230 for other processing, and completes the processing.

Figure 9:
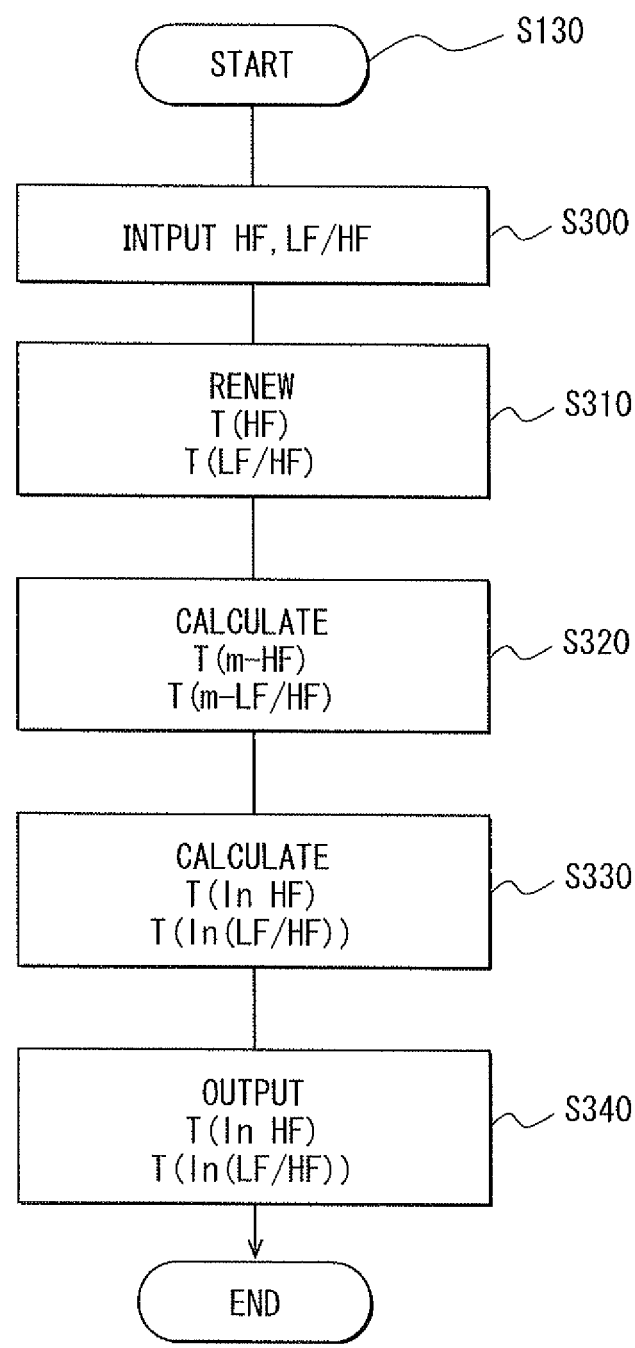
FIG. 9 is a flow chart showing a data processing.

Referring to FIG. 9, the data processing in the step S130 is explained in detail. In this processing, the apparatus calculates the time-based series data expressed by the natural logarithm, such as T(InHF) and T(In(LF/HF)) which are used for the abnormality determination.

As shown in FIG. 9, the apparatus inputs. HF and LF/HF in a step S300. In a following step S310, the apparatus renews and updates T(HF) and T(LF/HF) by adding the newly inputted data HF and LF/HF. T(HF) and T(LF/HF) are data for a predetermined period before the current time. The predetermined period means a time zone used for the abnormality determination, and corresponds to the monitoring period. In this embodiment, the monitoring period is 3 hours.

In a following step S320, the apparatus performs a moderating processing on T(HF) and T(LF/HF) in order to make the data moderate. In other words, the apparatus performs a moving average processing on T(HF) and T(LF/HF) in order to remove minor fluctuations which can be considered not to be related to the abnormality determination. For example, the apparatus calculates values of the moving average for data in every 10 minutes. Then, the apparatus stores the moving average values as time-based series data T(m-HF) and T(m-LF/HF).

In a following step S330, the apparatus calculates T(InHF) and T(In(LF/HF)) by transforming T(m-HF) and T(m-LF/HF) by using the natural logarithm.

Distribution of the values of T(HF) and T(LF/HF) is made to approximate to the normal distribution by using the natural logarithm. That is, although absolute values of LF/HF etc. are varied greatly in an up and down directions in individual cases, this transformation can make the individual differences small and enables it to compare those indexes correctly in a statistical manner.

In a following step S340, the apparatus stores and outputs T(InHF) and T(In(LF/HF)) and once completes the processing.

Figure 10:
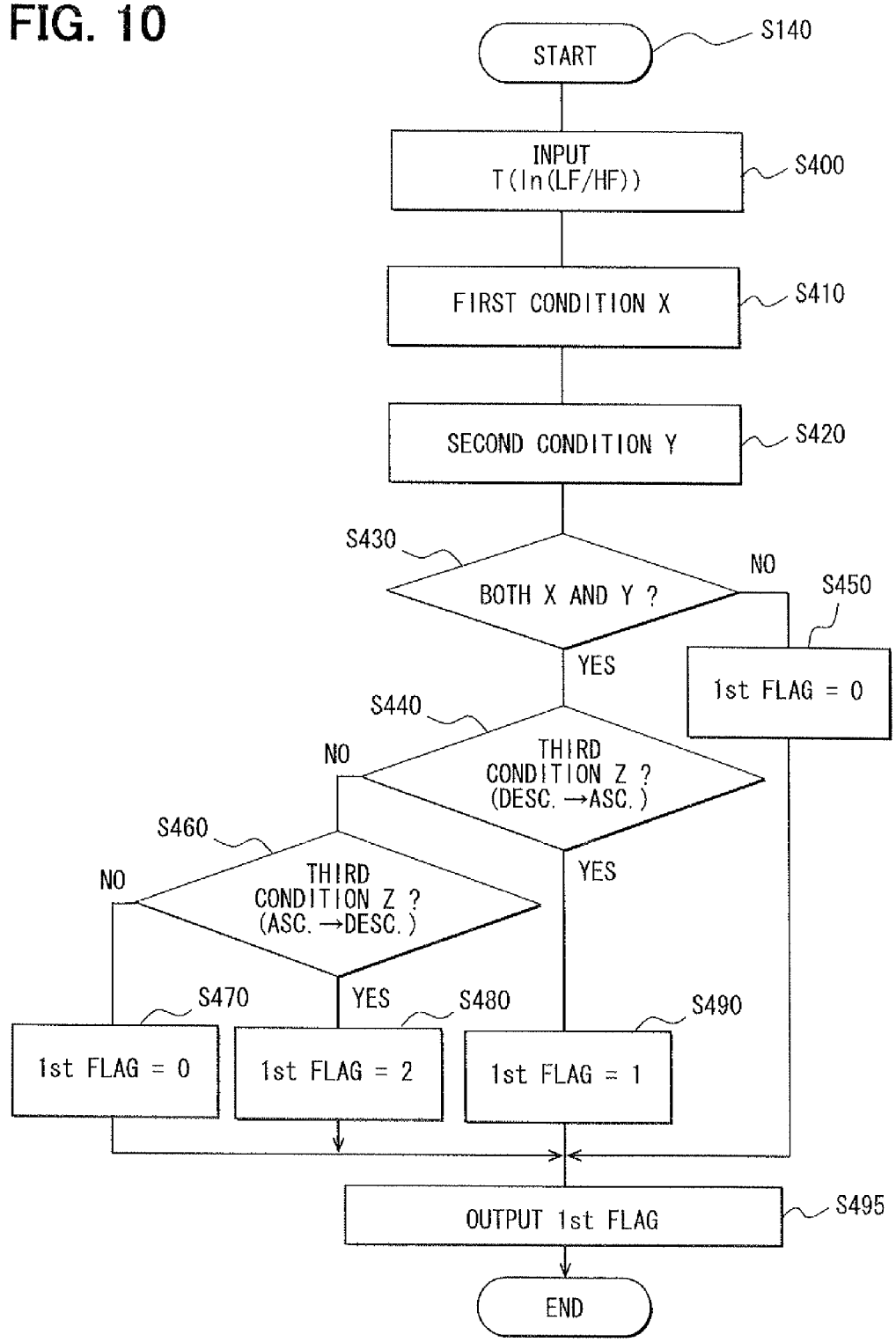
FIG. 10 is a flow chart showing an abnormality determination processing by using In(LF/HF)

Referring to FIG. 10, the evaluation processing for T(In(LF/HF)) in the step. S140 is explained in detail. As shown in FIG. 10, in a step S400, the apparatus inputs T(In(LF/HF)) which is transformed by the natural logarithm.

In a following step S410, the apparatus evaluates the amount of change in T(In(LF/HF)) in the referential period. That is, the apparatus determines that whether T(In(LF/HF)) satisfies the first condition "X" for the referential period.

In a following step S420, the apparatus evaluates the amount of change in T(In(LF/HF)) in the evaluation period. That is, the apparatus determines that whether T(In(LF/HF)) satisfies the second condition "Y" for the evaluation period. The apparatus determines that the second condition "Y" is satisfied only when a local minimum point or a local maximum point is detected within a half of the evaluation period.

In a following step S430, the apparatus determines that whether both the first condition "X" and the second condition. "Y" are satisfied or not. If an affirmative result "YES" is determined, there is a possibility that the driver will be suffered from a heart abnormality, therefore, the apparatus advances the routine to a step S440. On the other hand, if a negative result "NO" is determined, it is considered that the driver may not be suffered from the heart abnormality right now, therefore, the apparatus advances the routine to a step S450.

In the step S450, since there is no possibility of the heart abnormality as a result of the abnormality determination based on T(In(LF/HF)) the apparatus sets "0" on the first flag, and proceeds to a step S495.

On the other hand, in the step S440 since there is possibility of the heart abnormality, the apparatus determines that whether the value of T(In(LF/HF)) changes rapidly from a descending phase to an ascending phase in the evaluation period.

In detail, the apparatus determines that whether the third condition "Z" is satisfied or not. In detail, the apparatus determines that whether the extent of gradient of the index changing toward the ascending phase from the local minimum point can be considered as a steeper gradient that is equal to or greater than a predetermined threshold value. If an affirmative result "YES" is determined, the apparatus advances the routine to a step S490. On the other hand, if a negative result "NO" is determined, the apparatus advances the routine to a step S460. The apparatus determines that the third condition "Z" is satisfied only when an amount of change in the index in the ascending phase from the local minimum point is equal to or greater than a predetermined threshold value.

By this determination, it is possible to determine that whether the behavior of the index corresponds to the first abnormal-pattern shown in FIG. 3A or not.

In the step S490, it is a case in which the gradient of the regression line from the descending phase to the ascending phase corresponds to the abnormal pattern which suggests a heart abnormality, the apparatus sets "1" on the first flag to store and show the result, and proceeds to the step S495

On the other hand, in the step S460 to which the apparatus proceeds after the negative determination in a step S440, the apparatus determines that whether the value of T(In(LF/HF)) changes rapidly from the ascending phase to the descending phase in the evaluation period. By this determination based on the third condition "Z", it is possible to determine that whether the behavior of the index corresponds to the third abnormal-pattern shown in FIG. 5A or not.

In detail, the apparatus determines that whether the amount of change in the index is equal to or greater than a predetermined threshold and the extent of gradient of the index changing from the local maximum point can be considered as a steeper gradient that is equal to or greater than a predetermined threshold value. If an affirmative result "YES" is determined, the apparatus advances the routine to a step S480. On the other hand, if a negative judgment "NO" is determined, the apparatus advances the routine to a step S470.

In the step S480, it is a case in which the gradient of the regression line from the ascending phase to the descending phase corresponds to the abnormal pattern which suggests a heart abnormality, the apparatus sets "2" on the first flag to store and show the result, and proceeds to the step S495.

In the step S470, it is a case in which the gradient of the regression line is moderate, therefore, it is possible to consider that there is almost no possibility of the heart abnormality, the apparatus sets "0" on the first flag, and proceeds to the step S495.

In the step S495, the apparatus stores and outputs the result, such as the value of the first flag which is set in one of the steps S450, S470, S480, and S490, and once completes processing.

Figure 11:
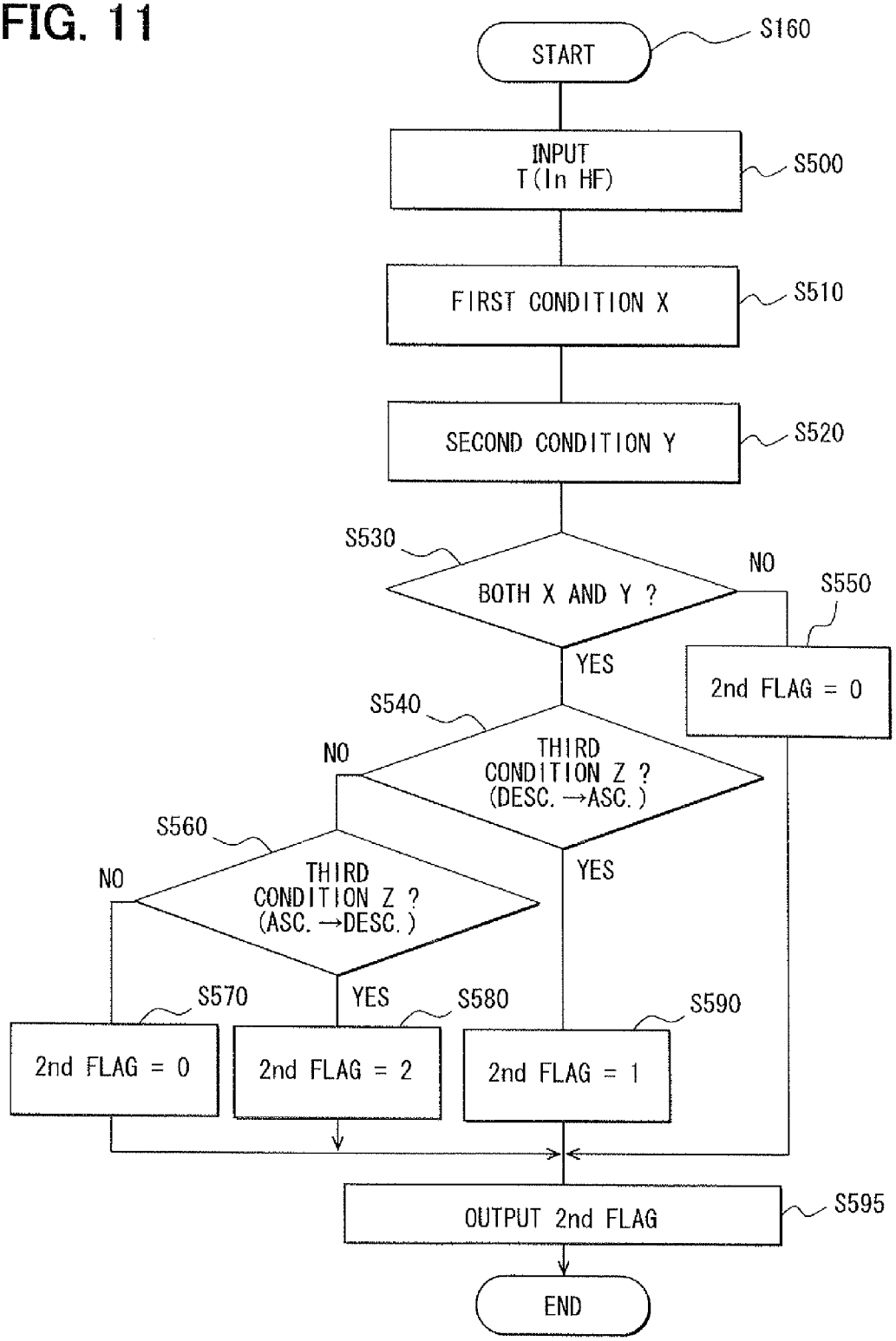
FIG. 11 is a flow chart showing an abnormality determination processing by using InHF.

Referring to FIG. 11 the evaluation processing on T(InHF) in the step S160 is explained in detail.

This evaluation processing performs an abnormality determination by using the data of T(InHF) similar to the step S140 in order to improve accuracy even higher after it is determined that the abnormality is determined as a result of the abnormality determination using the first flag in the step S150.

As shown in FIG. 11, in a step S500, the apparatus inputs T(InHF) which is transformed by the natural logarithm.

In a following step S510, the apparatus evaluates the amount of change in T(InHF) in the referential period. That is, the apparatus determines that whether T(InHF) satisfies the first condition "X" or not.

In a following step S520 the apparatus evaluates the amount of change in T(InHF) in the evaluation period. That is, the apparatus determines that whether T(InHF) satisfies the second condition "Y" or not. The apparatus determines that the second condition "Y" is satisfied only when a local minimum point or a local maximum point is detected within a half of the evaluation period.

In a following step S530, the apparatus determines that whether both the first condition "X" and the second condition "Y" are satisfied or not. If an affirmative result "YES" is determined, the apparatus advances the routine to a step S540. On the other hand, if a negative judgment "NO" is determined, the apparatus advances the routine to a step S550.

In the step S550, since there is no possibility of the heart abnormality as a result of the abnormality determination based on T(InHF), the apparatus sets "0" on a second flag, and proceeds to the step S495. The second flag indicates at least an existence or non-existence of an abnormality. The second flag can take three values, where "0" shows the non-existence of the abnormality, "1" and "2" show the existence of the abnormality. The second condition may be referred to as a second index abnormal flag or a T(InHF) abnormal flag.

On the other hand, in the step S540, since there is possibility of the heart abnormality, in order to improve accuracy of the determination even higher, the apparatus determines that whether the value of T(InHF) changes rapidly from a descending phase to an ascending phase in the evaluation period. By this determination, it is possible to determine that whether the behavior of the index corresponds to the third abnormal-pattern shown in FIG. 5A or not.

In detail, the apparatus determines that whether the third condition "Z" is satisfied or not. In detail, in a case that there is a predetermined amount of change in the index, the apparatus determines that whether the extent of gradient of the index changing toward the ascending phase from the local minimum point can be considered as a steeper gradient that is equal to or greater than a predetermined threshold value. If an affirmative result "YES" is determined, the apparatus advances the routine to a step S590. On the other hand, if a negative result "NO" is determined, the apparatus advances the routine to a step S560.

In the step S590, it is a case in which the gradient of the regression line from the descending phase to the ascending phase corresponds to the abnormal pattern which suggests a heart abnormality, the apparatus sets "1" on the second flag to store and show the result, and proceeds to a step S595.

On the other hand, in the step S560 to which the apparatus proceeds after the negative determination in the step S540, the apparatus determines that whether the value of T(InHF) changes rapidly from the ascending phase to the descending phase in the evaluation period. By this determination based on the third condition "Z", it is possible to determine that whether the behavior of the index corresponds to the first abnormal-pattern shown in FIG. 3B or not.

In detail, the apparatus determines that, when the amount of change in the index is equal to or greater than a predetermined threshold, whether the extent of gradient of the index changing from the local maximum point can be considered as a steeper gradient that is equal to or greater than a predetermined threshold value. If an affirmative result "YES" is determined, the apparatus advances the routine to a step S580. On the other hand, if a negative judgment "NO" is determined, the apparatus advances the routine to a step S570.

In the step S580, it is a case in which the gradient of the regression line from the ascending phase to the descending phase corresponds to the abnormal pattern which suggests a heart abnormality, the apparatus sets "2" on the second flag to store and show the result, and proceeds to the step S595

In the step S570, it is a case in which the gradient of the regression line is moderate, therefore, it is possible to consider that there is almost no possibility of the heart abnormality, the apparatus sets "0" on the first flag, and proceeds to the step S595.

In the step S595, the apparatus stores and outputs the result, such as the value of the second flag which is set in one of the steps S550, S570, S580, and S590, and once completes processing.

Figure 12:
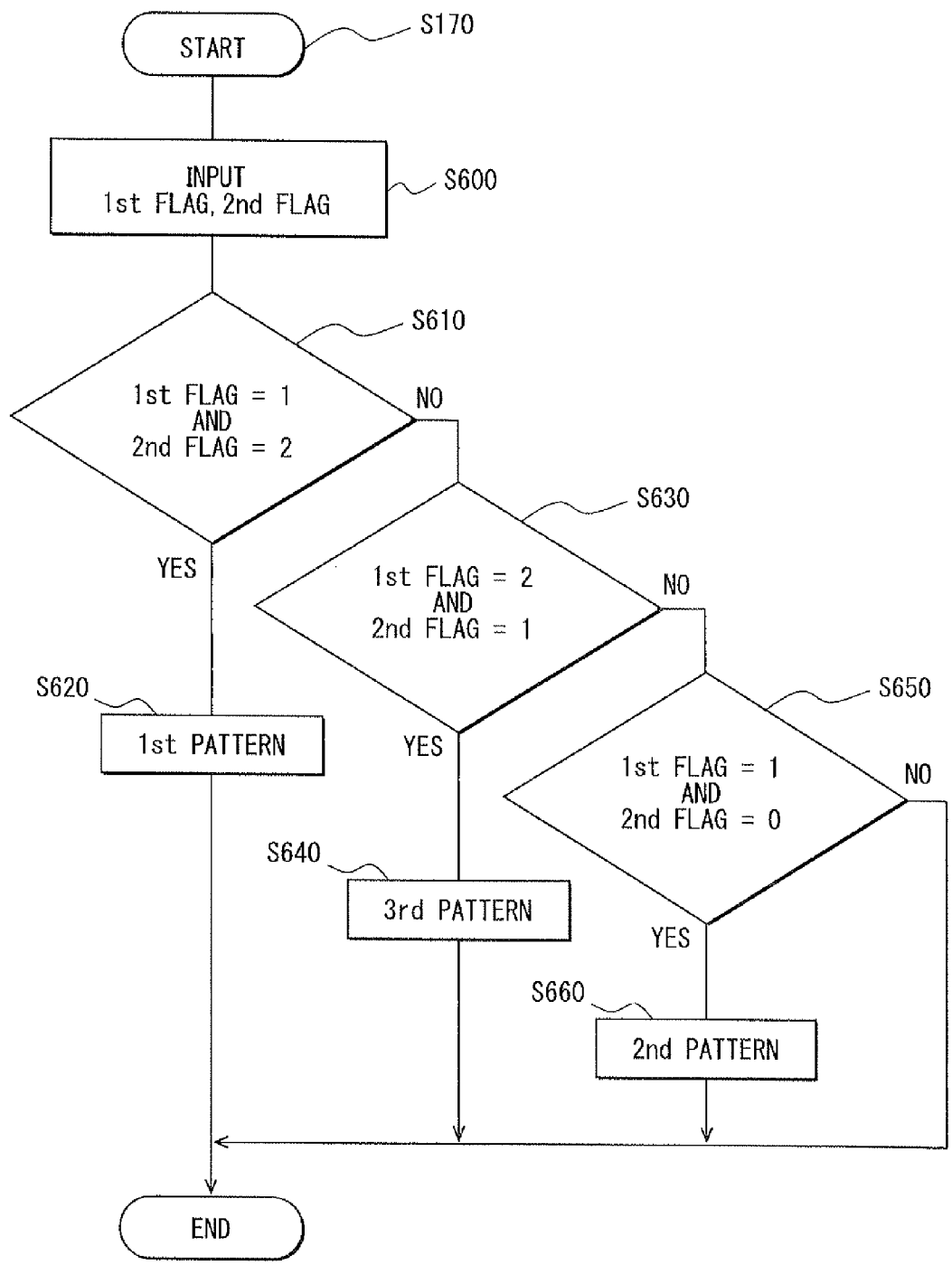
FIG. 12 is a flow chart showing an abnormal pattern determination processing.

Referring to FIG. 12, the evaluation processing for the abnormal patterns in the step S170 is explained in detail. As shown in the flow chart of FIG. 12, in a step S600 the apparatus inputs the value of the first flag and the value of the second flag.

In a following step S610, the apparatus determines that whether both conditions, the first flag is "1", and the second flag is "2", are satisfied or not. If an affirmative result "YES" is determined, the apparatus advances the routine to a step S620. On the other hand, if a negative judgment "NO" is determined, the apparatus advances the routine to a step S630.

In the step S620, since it is determined that the behaviors of the indexes corresponds to the first abnormal-pattern shown in FIG. 3A and FIG. 3B in the step S610, the apparatus once stores the determination result and completes the processing.

On the other hand, in the step. S630, the apparatus determines that whether both conditions, the first flag is "2", and the second flag is "1", are satisfied or not. If an affirmative result "YES" is determined, the apparatus advances the routine to a step S640. On the other hand, if a negative judgment "NO" is determined, the apparatus advances the routine to a step S650.

In the step S640, since it is determined that the behaviors of the indexes corresponds to the third abnormal-pattern shown in FIG. 5A and FIG. 5B in the step S630, the apparatus once stores the determination result and completes the processing.

On the other hand, in the step S650, the apparatus determines that whether both conditions, the first flag is "1", and the second flag is "0", are satisfied or not. If an affirmative result "YES" is determined, the apparatus advances the routine to a step S660. On the other hand, if a negative judgment "NO" is determined, since it is considered that there is no abnormality, the apparatus once completes the processing.

In the step S660, since it is determined that the behaviors of the indexes corresponds to the second abnormal-pattern shown in FIG. 4A and FIG. 4B in the step S650, the apparatus once stores the determination result and completes the processing.

According to the differences among the abnormal patterns, it is considered that there are higher possibilities to be suffered from the heart abnormality in the cases of the first abnormal-pattern and the third abnormal-pattern rather than that in the case of the second abnormal pattern.

The vehicle control processing, i.e., an action processing, in the step S180 is explained in detail.

In the step S180, the apparatus determines what kind of action, protective measure, shall be performed for the driver, a passenger, the vehicle or other vehicle on the traffic based on the determination result of the evaluating section 21, and outputs signals according to the determination to the vehicular controller 5, the storage device 7, the display device 9, and the communication device 11.

When the apparatus estimates that there is a certain level of probabilities of a heart abnormality in near further, and the apparatus determines that the driver is in the inappropriate condition for driving, the vehicular controller 5 performs at least one protective measure. For example, the vehicular controller 5 may automatically operate a brake device to apply braking force to the vehicle in a gradually increasing manner, and even to stop the vehicle. For example, the vehicular controller 5 may turn on a hazard lamp to be blinked in order to give cautions to the other vehicles on the traffic.

When the controlling section 23 determines that it is necessary to store data, the storage device 7 stores data, such as at least one of the electrocardiogram, RRI, HR, HF, LF/HF, and the determination result of the driver's biological condition.

The display device 9 displays the heart rate HR, the heartbeat interval variation HRV, and the determination result of the driver's biological condition.

In addition, in the case of the inappropriate condition for driving, the apparatus may output or display a warning message or advice to ask subjective symptoms. The apparatus may even output or displays a warning message, or advice to stop driving the vehicle depending on the case. Further, the apparatus may generate a voice message from an attached speaker, or turn on a warning lamp, such as LED, to be blinked.

Moreover, the communication device 11 may transmit an alarm signal to registered contacts, such as a medical institution and an emergency, or transmit position information of the vehicle to locate the vehicle.

As mentioned above, the apparatus in this embodiment evaluates behavior of the index, such as changing state of T(In(LF/HF)) and/or T(InHF), based on a frequency analysis of the heartbeat interval during driving the vehicle. Therefore, it is possible to detect and determine the inappropriate condition for driving, which corresponds to a symptom of a heart abnormality, based on the behavior of the index with sufficient accuracy. Since a heart abnormality can be detected in advance, the apparatus is very useful for the driver.

In the embodiment, the abnormality is determined by detecting only the R wave on the electrocardiogram. Therefore, it is possible to detect and determine the abnormality by a simple configuration and processing. It is not necessary to detect all of the P, Q, R and S waves. Therefore, it is possible to perform the abnormality determination easily in a noise environment, such as during driving a vehicle, in a comparison to a method in which an abnormality determination is performed by detecting all of the P, Q, R, S and T waves.

However, contrary to the advantage mentioned above, since the heartbeat interval variation HRV is a time-based fluctuation, it is necessary to collect a certain amount of data for a long time. Therefore, it is difficult to obtain a quick response. In addition, there is a characteristic that HRV does not contain such amount of information like the set of P, Q, R, S and T waves.

In order to address the above mentioned disadvantages, it is desirable to use the abnormality determination obtained by the heartbeat interval variation. HRV as a screening or triggering purpose.

In detail, if the apparatus determines the abnormality based on the heartbeat interval variation HRV, the apparatus does not make a final determination and outputs a question to ask subjective symptoms to the driver. For example, the apparatus outputs a question, such as "Don't you feel any abnormality on your heart?" via the display device 9, and inputs a driver's answer. Then, the apparatus finalizes the determination. If the driver's answer is "YES", which means the driver feels some abnormalities, the controlling section 23 of the apparatus determines the symptom of the heart abnormality and outputs the signal to the peripheral devices.

In addition, the apparatus may outputs advices to the driver to have at least one other measurement via the peripheral devices, such as the display device 9. The other measurement shall have a quick response and be performed in a stable condition in which the vehicle is stopped. For example, the apparatus may advice or suggest a blood-pressure measurement and a blood pressure abnormality determination based on the measured blood pressure, or an electrocardiograph measurement with detection of the P, Q, R, S, and T waves and the arrhythmic determination based on the measured waves. In addition, in a case that the apparatus includes a device capable of measuring waveforms of the electrocardiograph or a blood-pressure, the apparatus may automatically carry out the waveform measurement and/or the blood-pressure measurement.

Thereby, it is possible to provide an abnormality determination with higher accuracy and less incorrect determinations.

Further, if the symptom of the heart abnormality is determined, the apparatus may output an advice which suggests other biological measurement, e.g., a temperature and/or perspiration, other than that used in the abnormality determination. An image of a driver's face, an image of a driver's behavior, an image of a driver's posture, and a vehicle signal indicative of a vehicle behavior or operation are also useful indexes for determining an abnormality. Therefore, the apparatus may also use at least one of those indexes in addition to the ECG related indexes.

In the first embodiment, the driver condition evaluation apparatus 3 mounted on the vehicle performs the abnormality determination. However, the driver condition evaluation apparatus 3 may be configured as a distributed system having an external device which is not mounted on the vehicle. In such a system, the apparatus transmits the signal from the ECG sensor 1 to the external device by a wireless communication device and may perform the abnormality determination in the external device.

Second Embodiment

Hereinafter, other embodiments are explained. The following embodiments are modification of one of the preceding embodiments. Therefore, the same or similar components, parts and functions to the preceding embodiments are not repeatedly explained, and different components, parts and functions are mainly explained. A second embodiment is explained below.

In this embodiment, the apparatus evaluates and determines a grade of decreasing of the index during the evaluation period based on an amount of change in the index from the end of the referential period to a local minimum point, and a gradient of a regression line from the end of the referential period to the local minimum point. Then, the apparatus evaluates and determines a grade of increasing of the index in an ascending phase after completion of a descending phase based on an amount of change in increasing in the index from the local minimum point, and a gradient of a regression line from the local minimum point. The amount of change in increasing in the index from the local minimum point may be replaced with a predetermined fixed amount.

The apparatus evaluates and determines a grade of increasing of the index during the evaluation period based on an amount of change in the index from the end of the referential period to a local maximum point, and a gradient of a regression line from the end of the referential period to the local maximum point. Then, the apparatus evaluates and determines a grade of decreasing of the index in the descending phase after completion of the ascending phase based on an amount of change in decreasing in the index from the local maximum point, and a gradient of a regression line from the local maximum point. The amount of change in decreasing in the index from the local maximum point may be replaced with a predetermined fixed amount. The second embodiment can provide advantages similar to the first embodiment.

Third Embodiment

A third embodiment is explained below. In the embodiment, the biological condition evaluation apparatus is not configured as a vehicle mountable device. The biological condition evaluation apparatus is configured with a known electrocardiograph device, a general purpose computer, such as a personal computer, and peripheral devices, such as a display device and a storage device. The electrocardiograph device detects and monitors an electrocardiogram. The computer is installed with a program similar to the first embodiment. Therefore, the computer inputs the electrocardiogram, performs the abnormality determination similar to the first embodiment, and outputs the determination result to the storage device and the display device.

For example, in order to perform the abnormality determination, the biological condition evaluation apparatus may be provided by a Holter Electrocardiograph Recorder. For such a purpose, the program explained in the first embodiment can be modified to be executed by the Holter Electrocardiograph Recorder or other devices. For example, in order to perform the abnormality determination, the ECG sensor 1 and the program in the first embodiment may be modified and installed in a mobile phone or a wearable device capable of being carried all time.

For example, in order to perform the abnormality determination, the ECG sensor 1 and the program in the first embodiment may be modified and installed in a bedding article which contacts a human body for a long time, such as a bed mat type heart rate monitor device for a home use or a hospital use.

When the object human is in a time of beginning sleep, a time of amid sleep, or a time of getting up, there is a possibility of sharp and great change in the autonomic nerve activity. Such a change of the autonomic nerve activity in a sleep related period is sufficiently sharp and great to, cause the apparatus makes an error determination. In such sleep related periods, the apparatus may not be able to perform the abnormality determination with sufficient accuracy. Therefore, it is desirable to not adopt the determination result in such sleep related periods. In order to prevent such an error determination the apparatus further includes a sleep detecting device for detecting a sleep related period of the object human, and a section for preventing a final determination when the object human is in the sleep related period. The preventing section may be provided by the controlling section 23.

The sleep detecting device for detecting a time of beginning sleep, a time of amid sleep, or a time of getting up may be provided by well-known devices and techniques, such as a sleep-polygraph and an active-graph.

Fourth Embodiment

A fourth embodiment is explained below. Although the heartbeat interval is calculated based on the signal of the ECG sensor 1 in the first embodiment, the heartbeat interval may be estimated and calculated based on a pulse wave signal detected by a pulse wave sensor.

In this case, the heartbeat interval is not detected directly from the signal of the electrocardiograph. In this case, the heartbeat interval is detected indirectly from the pulse wave signal, since a pulse wave is originated in a heartbeat i.e., a heart rate.

After obtaining the heartbeat interval, the same processing of the frequency analysis and the abnormality determination as in the first embodiment can be used.

One of technologies for detecting or estimating a heartbeat interval from a heart pulse signal is disclosed in JP3729143B.

Other Embodiments

The present invention can take a form of the biological condition evaluation apparatus as explained in the embodiments. The present invention can take a form of an entirely hardware configuration, an entirely software configuration or a configuration containing both software and hardware elements.

The present invention can take a form of a computer executable program which causes a computer to perform the algorithm explained in the embodiments. The program may be stored in a computer readable storage medium.

The computer readable storage medium may be provided by known storage medium. For example, the computer readable storage medium may be a computer readable memory device, an electronic control unit configured as a microcomputer system, a micro-chip, a flexible disk, a hard disk, and an optical disk.

The computer program may be transmitted to the computer readable storage medium via a communication medium, such as the internet.

Although the present invention has been fully described in connection with the preferred embodiments thereof with reference to the accompanying drawings, it is to be noted that various changes and modifications will become apparent to those skilled in the art. Such changes and modifications are to be understood as being within the scope of the present invention as defined by the appended claims.

What is claimed is:

1. An apparatus for evaluating biological condition, which determines a symptom of a heart abnormality based on biological information that is at least one of a heartbeat interval and a pulse interval, the apparatus comprising:

means for calculating an index by performing a frequency analysis on at least one of the heartbeat interval and the pulse interval, the index being indicative of the sympathetic nerve activity;

means for determining whether the index is in a referential period, which is a time period in which the index satisfies a predetermined condition which shows that an amount of change in the index calculated in the index calculating means is smaller than a predetermined reference threshold value over a predetermined period; and means for determining a symptom of a ventricular fibrillation after the predetermined condition for the referential period is satisfied, the symptom being determined when the following both conditions (1) and (2) are satisfied during an evaluation period which is set after the referential period, (1) both amounts of change in the index in an increasing direction and a decreasing direction are equal to or greater than respective predetermined amount threshold values which indicate that the amount of change is greater than an amount of change in the index observed during the referential period, and (2) both rates of change in the index in the increasing direction and the decreasing direction are equal to or greater than respective predetermined rate threshold values, wherein the symptom of the ventricular fibrillation is determined when the index changes rapidly from the decreasing direction to the increasing direction in the evaluation period.

2. The apparatus for evaluating biological condition according to claim 1, wherein the index is expressed by the natural logarithm.

3. The apparatus for evaluating biological condition according to claim 1, wherein the predetermined condition for determining the referential period is that the change in the index is equal to or smaller than the predetermined reference threshold value.

4. The apparatus for evaluating biological condition according to claim 1, wherein the respective predetermined amount threshold value for the amount of change in the index is a value of mean (index)±1SD, where the mean(index) is an average value of the index in the referential period, and 1SD is a unit of the standard deviation of the index in the referential period.

5. The apparatus for evaluating biological condition according to claim 1, wherein the respective predetermined amount threshold value for the amount of change in the index is a variable according to the absolute value of the index in the referential period.

6. The apparatus for evaluating biological condition according to claim 1, wherein the referential period is defined by using past data of the index.

7. The apparatus for evaluating biological condition according to claim 1, wherein the abnormality determining means determines that the condition (1) for the amount of change in the index is satisfied when the amount of change in the index in the evaluation period is within a range from mean(index) ±1.5SD to mean(index)±3.0SD, where the mean(index) is an average value of the index in the referential period, and SD is the standard deviation of the index in the referential period.

8. The apparatus for evaluating biological condition according to claim 1, wherein the abnormality determining means performs the determination based on a gradient of a regression line of the index during the evaluation period.

9. The apparatus for evaluating biological condition according to claim 8, wherein the determination using the gradient of the regression line is performed by comparing the gradient of the regression line with a predetermined variable gradient threshold value that is variable according to the absolute value of the index during the referential period.

10. The apparatus for evaluating biological condition according to claim 8, wherein
the abnormality determining means changes an abnormal grade showing a grade of the abnormality according to a grade of the gradient of the regression line.

11. The apparatus for evaluating biological condition according to claim 1, wherein
the index calculating means calculates a first index that is the index indicative of the sympathetic nerve activity and a second index indicative of the parasympathetic nerve activity,
the referential period determining means and the abnormality determining means determine the symptom of the heart abnormality based on both of the indexes respectively, and
the abnormality determining means determines a final result of determination when the abnormality determining means determines that both the first and second indexes indicate the symptom of the ventricular fibrillation respectively.

12. The apparatus for evaluating biological condition according to claim 1, wherein
the index calculating means calculates a first index that is the index indicative of the sympathetic nerve activity and a second index indicative of the parasympathetic nerve activity,
the referential period determining means and the abnormality determining means determine the symptom of the ventricular fibrillation based on both of the indexes respectively, and
the abnormality determining means determines an abnormal pattern which is used for the determination by adding a condition in which the first index and the second index change in opposite increasing and decreasing directions.

13. The apparatus for evaluating biological condition according to claim 1, wherein
the abnormality determining means avoids determining the symptom when the abnormality determining means determines that a human which is evaluated for by the apparatus for a biological condition is in a time of beginning sleep, a time of amid sleep, or a time of getting up.

14. The apparatus for evaluating biological condition according to claim 1, wherein
the apparatus is able to be mounted on a vehicle.

15. The apparatus for evaluating biological condition according to claim 1, wherein
the determination is carried out when the vehicle is driven.

16. The apparatus for evaluating biological condition according to claim 1, further comprising:
a sensor which detects biological condition, an output device which outputs an announcement corresponding to the result of the determination, and
a control device which performs control according to the result of the determination, wherein
the sensor performs, in response to the determination of the symptom, at least one measurement among an electrocardiograph measurement, a blood-pressure measurement, and other biological measurement different from one that is used in the determination, and wherein
the output device performs, in response to the determination of the symptom, at least one output among an announcement output suggesting other abnormality determination different from one that is used in the determination, an announcement output asking subjective symptoms, an announcement output suggesting an electrocardiograph measurement, an announcement output suggesting a blood-pressure measurement and an announcement output suggesting other biological measurement different from one that is used in the determination.

17. A method for evaluating biological condition, which determines a symptom of a heart abnormality based on biological information that is at least one of a heartbeat interval and a pulse interval, the method comprising the steps of:
calculating an index with a microcomputer by performing a frequency analysis on at least one of the heartbeat interval and the pulse interval, the index being indicative of the sympathetic nerve activity;
determining, with the microcomputer, whether the index is in a referential period, which is a time period in which the index satisfies a predetermined condition which shows that an amount of change in the index calculated in the index calculating step is smaller than a predetermined reference threshold value over a predetermined period; and
determining, with the microcomputer, a symptom of a ventricular fibrillation after the predetermined condition for the referential period is satisfied, the symptom being determined when the following both conditions (1) and (2) are satisfied during an abnormality evaluation period which is set after the referential period,
(1) both amounts of change in the index in an increasing direction and a decreasing direction are equal to or greater than respective predetermined amount threshold values which indicate that the amount of change is greater than an amount of change in the index observed during the referential period, and
(2) both rates of change in the index in the increasing direction and the decreasing direction are equal to or greater than respective predetermined rate threshold values,
wherein the symptom of the ventricular fibrillation is determined when the index changes rapidly from the decreasing direction to the increasing direction in the evaluation period.

18. The method according to claim 17, wherein
the index calculating step calculates a first index that is the index indicative of the sympathetic nerve activity and a second index indicative of the parasympathetic nerve activity,
the referential period determining step and the symptom determining step determine the symptom of the heart abnormality based on both of the indexes respectively, and
the symptom determining step determines a final result of determination when the symptom determining step determines that both the first and second indexes indicate the symptom of the ventricular fibrillation respectively.

19. The method according to claim 17, wherein the index calculating step calculates a first index that is the index indicative of the sympathetic nerve activity and a second index indicative of the parasympathetic nerve activity,
the referential period determining step and the symptom determining step determine the symptom of the ventricular fibrillation based on both of the indexes respectively, and
the symptom determining step determines an abnormal pattern which is used for the determination by adding a condition in which the first index and the second index change in opposite increasing and decreasing directions.

20. A non-transitory computer-readable medium comprising a computer program that, when executed on a computer, causes the computer to perform the method of claim 17.

* * * * *